(12) United States Patent
Yamamoto et al.

(10) Patent No.: US 7,109,014 B1
(45) Date of Patent: Sep. 19, 2006

(54) DIGLYCOSIDASE ISOLATED FROM MICROORGANISMS

(75) Inventors: Shigeru Yamamoto, Aichi (JP); Masamichi Okada, Aichi (JP); Taichi Usui, Shizuoka (JP); Kanzo Sakata, Kyoto (JP); Atsuki Toumoto, Aichi (JP); Kazutaka Tsuruhami, Aichi (JP)

(73) Assignee: Amano Enzyme Inc., Aichi (JP)

( * ) Notice: Subject to any disclaimer, the term of this patent is extended or adjusted under 35 U.S.C. 154(b) by 0 days.

(21) Appl. No.: 09/806,413

(22) PCT Filed: Sep. 29, 1999

(86) PCT No.: PCT/JP99/05346

§ 371 (c)(1),
(2), (4) Date: Mar. 30, 2001

(87) PCT Pub. No.: WO00/18931

PCT Pub. Date: Apr. 6, 2000

(30) Foreign Application Priority Data

Sep. 30, 1998 (JP) .................... 10/294675

(51) Int. Cl.
*C12N 9/26* (2006.01)

(52) U.S. Cl. ..................................... 435/201
(58) Field of Classification Search ................ 435/201, 435/203, 71.1, 71.2
See application file for complete search history.

(56) References Cited

U.S. PATENT DOCUMENTS

| | | | |
|---|---|---|---|
| 5,726,034 A | | 3/1998 | Bryan et al. |
| 5,789,581 A | | 8/1998 | Matsuura et al. |
| 5,827,682 A | | 10/1998 | Bryan et al. |
| 6,020,540 A | * | 2/2000 | Harman et al. ............ 800/302 |
| 2003/0194469 A1 | | 10/2003 | Tsuruhami et al. |

FOREIGN PATENT DOCUMENTS

| | | |
|---|---|---|
| JP | 8-140675 | 6/1996 |
| JP | 8-214787 | 8/1996 |
| JP | 11-89589 | 4/1999 |
| WO | WO 95/10512 A1 | 4/1995 |
| WO | WO 95/10530 A1 | 4/1995 |
| WO | WO 00/18931 A1 | 4/2000 |

OTHER PUBLICATIONS

McCormack et al., Biotechnol Lett 13(9):677-682 (1991).*
Biochemistry, 2nd Ed., Voet et al., 1995, John Wiley and Sons, Inc., New York.*
Fundamentals of Organic Chemistry, 3rd Ed., Solomons, 1990, John Wiley and Sons, Inc., New York.*
American Heritage Dictionary 4th Ed., 2000.*
Branden et al., "Introduction to Protein Structure", Garland Publishing Inc., New York, 1991.*
Narikawa et al. (2000) Biosci Biotechnol Biochem 64:1317-1319.*
Witkowski et al. (1999) Biochemistry 38:11643-11650.*
Yasuyuki Ijima, et al "Characterization of β-primeverosidase, being concerned with alcoholic aroma formation in tea leaves to be processed into black tea, and preliminary observations on its substrate", J. Agric. Food Chem. (May, 1998), vol. 46, No. 5, pp. 1712-1718.
Yin Kiong Hoh et al., "Properties of β-glucosidase purified from Aspergillus niger mutants USDB 0827 and USDB 0828", Applied Microbiology Biotechnology (1992), vol. 37, No. 5, pp. 590-593.
Wolfgang Hosel "Reinigung und charaketerisierung zwier β-glykosidasen mit bevorzutgter spezifitat fur biochanin-A-7-β-apiosylglucosid aus Cicer arietinum L" Hoppe-Seyler's Z. Physiol. Chem. (1976), vol. 357, No. 12, pp. 1673-1681.
Hosel, W., "Purification and Properties of 2-Beta Glycosidases from Cicer-Arietinum with Preferential Specificity for Biochanin A 7-Beta Apiosyl Glucoside," Hoppe-Seyler's Z. Physiol. Chem. Bd., vol. 357, No. 12, pp. 1673-1681, Dec. 1976.
Wenfei, G., et al., "A Primeverosidase as Main Glycosidase Concerned with the Alcoholic Aroma Formation in tea leaves," Biosci. Biotech. Biochem., vol. 59, No. 5, pp. 962-964, 1995.
Weifei, G., et al., "Isolation and Characterization of a β-Primeverosidase Concerned with Alcoholic Aroma Formation in Tea Leaves," Biosci. Biotech. Biochem., vol. 60, No. 11, pp. 1810-1814, 1996.
Ogawa, K., et al., "Purification of a β-Primeverosidase Concerned with Alcoholic Aroma Formation in Tea Leaves (Cv. Shuixian) To Be Processed to Oolong Tea," J. Agric Food Chem., vol. 45, No. 3, pp. 877-882, 1997.
Ichigo, H., et al., "Summary of the Studies on the Scent Evolution During Flower Opening," Fragrance Journal, vol. 27, No. 2, pp. 21-27, Feb. 1999.
Sakata, K., et al., "Beta-Primeverosidase Concerned with the Floral Tea Aroma Formation During Processing of Oolong Tea and Black Tea," Abstracts of Papers American Chemical Society, vol. 217, No. 1-2, pp. 77, 1999.
Spielman, L. L., et al: "A Specific Stain for 18-20 α-Glucosidases in Isoelectri Focusing Gels" Analytical Biochemistry, vol. 120, No. 1, 1982 pp. 66-70, XP009000499.
Mach, R. L., et al.: "The bgl1 gene of Trichoderma reesei QM 9414 encodes an extracellular, cellulose-inducible β-glucosidase involved in cellulase induction by sophorose" Molecular Biology, Blackwell Scientific, Oxford, GB, vol. 16, No. 4, May 1995, pp. 687-697, XP001080361.

(Continued)

*Primary Examiner*—David J. Steadman
(74) *Attorney, Agent, or Firm*—Sughrue Mion, PLLC

(57) ABSTRACT

This invention relates to a novel microorganism-derived enzyme having an activity to cut disaccharide glycosides (particularly, β-primeveroside and/or analogous disaccharide glycosides) in disaccharide unit, a method for producing the enzyme, a gene which encodes the enzyme and use of the enzyme. Various components can be formed by the action of this enzyme upon disaccharide glycosides.

2 Claims, No Drawings

OTHER PUBLICATIONS

Kan, V. L. et al.: "β1,4-Oligoglucosides Inhibit the Binding of *Aspergillus fumigatus* Conidia to Human Monocytes" Journal of Infectious Diseases, Chicago, IL, US, vol. 163, No. 5, Jan. 1991, pp. 1154-1156, XP001079462.

Matsuura, et al., "B-Glucosidases from Soybeans Hydrolyze Daidzin and Genistin." Journal of Food Science, vol. 58, No. 1, pp. 144-147, 1993.

Hoesel et al., "Development and distribution of isoflavone-O-Beta glycoside specific beta glycosidases in Cicer-arietinum." Planta Medica (1976) vol. 30, No. 2, pp. 97-103.

Hösel, W., et al.: "β-Glucosidases from *Cicer arietinum* L., Purification and Properties of Isoflavone-7-O-glucoside-Specific β-Glucosidases", Eur. J. Biochem., vol. 57, (1975), pp. 607-616.

Hösel, W.: "Glycosylation and Glycosidases", The Biochemistry of Plants, vol. 7, (1981), pp. 725-753.

Hay, G. W., et al.: "Degradation of rutin by aspergillus flavus. Purification and characterization of rutinase" Can. J. Microbiol., vol. 7 (1961), pp. 921-932.

Bokkenheuser, V. D., et al.: "Hydrolysis of flavonoids by human intestinal bacteria", Plant Flavonoids in Biology and Medicine II: Biochemical, Cellular, and Medicinal Properties, Alan R. Liss, Inc., (1988), pp. 143-145.

Suzuki, H.: "Hydrolysis of flavonoid glycosides by enzymes (rhamnodiastase) from rhamnus and other sources", Archives of Biochemistry and Biophysics, vol. 99, (1962), pp. 476-483.

\* cited by examiner

DIGLYCOSIDASE ISOLATED FROM MICROORGANISMS

TECHNICAL FIELD

This invention relates to a novel microorganism-derived enzyme having an enzyme activity to cut disaccharide glycosides, particularly β-primeveroside and/or its analogs, in disaccharide unit, a method for producing said enzyme, a gene which encodes said enzyme, a vector containing said gene, a transformant transformed with said vector and use of said enzyme.

BACKGROUND ART

Alcoholic aromas such as geraniol, linalool, benzyl alcohol, 2-phenyl alcohol and $C_{13}$-norterpenoid alcohol as plant aroma components take an important role in the aroma formation of, for example, flowers, tea, fruits and wine.

Among these aroma components, monosaccharide glycosides such as β-D-glucopyranoside have been isolated and identified as aroma precursors of benzyl alcohol and (Z)-3-hexenol.

Recently, the presence of a disaccharide glycoside β-primeveroside (6-O-β-D-xylopyranosyl-β-D-glucopyranoside) or its analogs has been confirmed as precursors of fragrant alcohols such as geraniol and linalool, which seem to be taking an important role regarding the aroma of flowers. The presence of the disaccharide glycoside β-primeveroside and its analogs has also been revealed as precursors of other alcoholic aroma components described above.

In addition to such aromas, the presence of the disaccharide glycoside β-primeveroside or its analogs has also been found in certain physiologically active substances such as pigments and pharmacological components. For example, it is known that macrozamin in a cycad, etc. is cut by β-primeverosidase in disaccharide unit to form a toxin.

On the other hand, such an enzyme having a function to cleave precursors of these aroma components and physiologically active components in disaccharide unit has been confirmed only in a small amount in, for example, tea leaves (JP-A-8-140675; the term "JP-A" as used herein means an "unexamined published Japanese patent application"), and almost no study on its application has been carried out. Recently, it became apparent that the aglycon cannot be sufficiently released from these disaccahride glycoside and analogues thereof by the action of the known glucosidase. In consequence, great concern has been directed toward the development of a method by which such an enzyme can be produced on an industrial scale at low cost without depending on the prior art supply sources such as tea leaves.

DISCLOSURE OF THE INVENTION

With the aim of solving the aforementioned problems, the inventors of the present invention have conducted intensive studies searching for its supply source in microorganisms. That is, as a result of efforts to screen a microorganism capable of producing an enzyme having the aforementioned function from a broad range of natural sources, we have found a microorganism which is suitable for fermentation culturing and has the ability to produce an enzyme having the action to cut the saccharide moiety of disaccharide glycosides such as β-primeveroside in disaccharide unit, and have isolated and purified said enzyme and determined nucleotide sequence of a gene that encodes said enzyme. Thereafter, we have found the enzyme having the aforementioned action in a large number of microorganisms such as molds, yeast, bacteria and actinomycetes and thereby accomplished this invention.

Accordingly, the invention relates to a novel microorganism-derived enzyme having an enzyme activity to cut disaccharide glycosides, particularly β-primeveroside and/or its analogs, in disaccharide unit, a method for producing said enzyme, a gene which encodes said enzyme, a vector containing said gene, a transformant transformed with said vector and use of said enzyme.

The enzyme of the present invention is characterized in that it has an activity to release saccharides in a disaccharide unit from the disaccharide glycoside by acting on the disaccharide glycoside which can hardly be utilized as the substrate by the known glycosidase. In the present specification, the enzyme having such activity is called "diglycosidase". The diglycosidase of the present invention has not only the activity to act on the disaccharide glycoside to release the saccharides in a disaccharide unit but also cut the glycoside bonding of the monoglycoside. Moreover, it has an activity to cut the glycoside bonding of the modified monoglycoside (e.g., acetylglucoside, malonylglucoside, methylglucoside, phosphoglucoside, and amidoglucoside).

The microorganism-derived enzyme of the present invention which has the activity to act upon a disaccharide glycoside and thereby release saccharides in disaccharide unit from said disaccharide glycoside is different from the plant-derived enzyme in terms of physicochemical properties and homology of gene sequences.

Next, the present invention is described in detail.

In this connection, results of the measurement of various enzyme activities carried out in the present invention are shown by values obtained by the following methods unless otherwise noted.

(1) Disaccharide Glycoside Degradation Activity

Measurement of the activity was carried out using an automatic chemical analyzer (TBA-30R, manufactured by TOSHIBA CORP.). A 30 μl portion of each enzyme sample was mixed with 200 μl of acetate buffer solution (pH 5.5) containing 2 mM of p-nitrophenyl (pNP) primeveroside as the disaccharide glycoside substrate to carry out the reaction at 40° C. and at a cycle time of 22.5 seconds, for 9.75 minutes, and then the reaction solution was mixed with 250 μl of sodium carbonate to measure absorbance at 412 nm. Measurement of the sample blank was carried out in the same manner using 20 mM acetate buffer (pH 5.5) instead of the substrate solution.

One unit of the enzyme activity is defined as the amount of enzyme which increases the absorbance by a factor of 1 under these conditions.

The pNP-primeveroside used herein can be synthesized for example by allowing pNP-glucoside (manufactured by Merck) to react with xylo-oligosaccharide (manufactured by Wako Pure Chemical Industries) using an enzyme xylosidase (manufactured by Sigma), thereby effecting transfer of one xylose residue to pNP-glucoside through β-1,6-bonding.

(2) β-Glucosidase Activity

Measurement of the activity was carried out using an automatic chemical analyzer (TBA-30R, manufactured by TOSHIBA CORP.). A 10 μl portion of each enzyme sample was mixed with 200 μl of acetate buffer solution (pH 5.5) containing 2 mM of p-nitrophenyl (pNP) glucoside as the substrate to carry out the reaction at 40° C. and at a cycle time of 22.5 seconds, and then the reaction solution was mixed with 250 μl of sodium carbonate to measure absorbance at 412 nm. Measurement of the sample blank was carried out in the same manner using 20 mM acetate buffer (pH 5.5) instead of the substrate solution.

One unit of the enzyme activity is defined as the amount of enzyme which increases the absorbance by a factor of 1 under these conditions.

In order to obtain a microorganism capable of producing an enzyme having a diglycosidase activity, the present inventors have examined a broad range of natural sources and found that several microbial strains isolated from the natural world can produce an enzyme having said activity. The disaccharide glycosides analogous to β-primeveroside are disaccharides glycosides having glucose on the aglycon side, such as apiofuranosyl-β-D-glucopyranoside and arabinofuranosyl-β-D-glucopyranoside.

The diglycosidase producing microorganisms of the present invention can be screened, for example, in the following manner. That is, a soil sample solution is inoculated into a separation liquid medium containing eugenyl-primeveroside or the like compound as the sole carbon source to carry out enrichment culturing, the resulting culture broth is spread on a separation agar plate medium having the same composition, and the thus grown colonies are selected and isolated. A strain having an activity to release pNP from bypassing disaccharide (e.g., pNP-primeveroside or the like) can be selected by culturing the thus isolated strains in an appropriate liquid medium.

A diglycosidase producing microorganism can be screened from the thus selected strains using pNP-primeveroside or the like compound as the substrate and release of disaccharide as the index.

Main strains isolated by the present inventors were identified by examining their mycological properties in the light of the following references (1) to (3).

REFERENCES (1) Raper, K. B. and Fennell, D. I., 1965. "The genus *Aspergillus*", Williams & Wilkins, Baltimore.
(2) Kozakiewicz, Z., 1989. *Aspergillus* species on stored products. Mycological Papers, No. 161, CAB International Mycological Institute.
(3) Al-Musallam, A., 1980. "Revision of the black *Aspergillus* species", University of Utrecht.

Mycological properties are described in the following.

Identification of Strain A (1) Growth Condition

Growth Condition
  Czapek Agar Medium
  Colony size is 48 to 50 mm in diameter (25° C., 7 days), its surface is velutinous to powdery, hypha is white, formation of conidia is slightly poor, dull green to grayish green, backside is light yellowish brown to brown.
  Malt Extract Agar Medium
  Colony size is 78 to 80 mm in diameter (25° C., 7 days), its surface is velutinous powdery, hypha is white, formation of conidia is markedly good, dull green to grayish green, backside is colorless to yellowish white. Colony size at 37° C. (3 days) is 73 to 75 mm in diameter. Good growth even at 45° C.

(2) Morphology
  Conidial Heads:
  Strong columnar form, 48 to 128 µm in length, 16 to 52 µm in diameter, dull green to grayish green.
  Conidiophores:
  Forms from substrate mycelium, 125 to 800 µm in length (mostly 500 µm or less), 5 to 10 µm in diameter, straight or slight bending, smooth surface.
  Vesicles:
  Diameter from 10 to 25 µm, flask shape, forms phialide in upper ⅔.
  Metulae:
  Not formed.
  Phialides:
  5.6~12×2.4~3.2 µm
  Conidia:
  Diameter from 2.6 to 3.6 µm, globose to subglobose, echinulate surface.
  Ascospores:
  Not formed.

The above results show that the strain A belongs to the *Aspergillus fumigatus* group, because the conidium forming cells are single columnar (metula is not formed), the conidial head is cylindrical and dull green to grayish green, the conidia are globose and ascospore is not formed. In addition, since the conidial head is strong columnar and does not form nodding appearance, the conidia have echinulate surface and most of the conidiophores are 500 µm or less, this strain is *Aspergillus fumigatus*.

Identification of Strains B, C and D (1) Growth Condition

TABLE 1

| Medium | Item | Strain B | Strain C | Strain D |
|---|---|---|---|---|
| Czapek agar medium | Colony diameter (25° C., 7 days) | 45 to 48 mm | 47 to 50 mm | 46 to 48 mm |
| | Colony diameter (25° C., 14 days) | 80 mm or more | 80 mm or more | 80 mm or more |
| | Hyphae layer | dense, white to yellow | dense, white | dense, white |
| | Formation of conidia | good | good | good |
| | Color of conidia | dull grayish brown to black brown | dull grayish brown to black brown | dull grayish brown to black brown |
| | Backside color | white to yellow | white | white |
| Malt extract agar medium | Colony diameter (25° C.) | 46 to 51 mm | 53 to 55 mm | 55 to 59 mm |
| | Hyphae layer | thin and flat, colorless | thin and flat, colorless | thin and flat, colorless |
| | Formation of conidia | very good | very good | very good |
| | Color of conidia | black to black brown | black to black brown | black to black brown |
| | Backside color | colorless | colorless | colorless |

(2) Morphology (Czapek Agar Medium)

TABLE 2

| Item | | Strain B | Strain C | Strain D |
|---|---|---|---|---|
| Conidial heads | Shape | spherical, radial, sometimes split into cylindrical form when matured | spherical, radial, sometimes split into cylindrical form when matured | spherical, radial, sometimes split into cylindrical form when matured |
| | Size | 120 to 560 µm | 150 to 500 µm | 125 to 350 µm |
| | Color | dull grayish | dull grayish brown | dull grayish |

TABLE 2-continued

| Item | | Strain B | Strain C | Strain D |
|---|---|---|---|---|
| | | brown to black brown | to black brown | brown to black brown |
| Conidio-phores | Origin | forms from substrate mycelium | forms from substrate mycelium | forms from substrate mycelium |
| | Length | 350 μm to 3 mm | 350 μm to 3 mm | 350 μm to 2.5 mm |
| | Diameter | 9 to 20 μm | 10 to 22.5 μm | 12.5 to 20 μm |
| | Surface | smooth | smooth | smooth |
| Vesicles | Diameter | 20 to 80 μm | 15 (mostly 35) to 80 μm | 30 to 80 μm |
| | Shape | globose | globose | globose |
| | Metula formation region | entire | entire | entire |
| Metulae | Length | 20 to 24 μm | 12 to 22.4 μm | 12.8 to 24 μm |
| | Diameter | 5.6 to 7.2 μm | 4.8 to 6.8 μm | 5.6 to 8 μm |
| | Shape | globose to subglobose | globose to subglobose | globose to subglobose |
| | Surface | echinulate | echinulate | echinulate |
| Ascospore | | not formed | not formed | not formed |

Based on the above results, all of the strains B, C and D belong to the *Aspergillus niger* group, because the conidia forming cells are double columnar (metulae and phialides are formed) and the conidial heads are globose and blackish. In addition, since the colony diameter becomes 5 cm or more by 14 days on the Czapek agar medium, the conidial surface is echinulate (verrucose), the conidium is globose to sub-globose shape of 6 μm or less and dull grayish brown to black brown and the conidiophore is 6 μm or less, these are strains of *Aspergillus niger* var. *niger*.

The present inventors also have selected strains belonging to the genus *Aspergillus* from type cultures at random and examined their ability to produce diglycosidase. As a result, productivity of the enzyme was also found, for example, in *Aspergillus niger* IFO 4407, *Aspergillus niger* IAM 2020 and *Aspergillus fumigatus* IAM 2046, etc. In addition, screening of various other microorganisms was also carried out for their ability to produce diglycosidase. As a result, the diglycosidase activity was found in various microorganisms such as those belonging to the genus *Aspergillus*, the genus *Penicillium*, the genus *Rhizopus*, the genus *Rhizomucor*, the genus *Talaromyces*, the genus *Mortierella*, the genus *Cryptococcus*, the genus *Microbacterium*, the genus *Corynebacterium* and the genus *Actinoplanes*.

The strains which can be used in the present invention are not limited to the strains described above, and any strain having diglycosidase productivity can be used. In addition, mutants of the strains having diglycosidase productivity, or various microorganisms or various cells (e.g., yeast cells, bacterial cells, higher plant cells and animal cells) modified by recombinant DNA techniques to have an ability to produce diglycosidase, in particular, preferably those modified to produce diglycosidase in great quantity are also included in the production method which can be used in the present invention. When diglycosidase productivity is added by introducing a diglycosidase gene, the host microorganism may not have the diglycosidase productivity.

When diglycosidase is produced using the aforementioned various microorganisms, methods and conditions suited for the culturing of said microorganisms can be selected, and such methods and conditions are not particularly limited. For example, culturing method of the aforementioned various strains may be either liquid culturing or solid culturing, but liquid culturing is preferably used. For example, the liquid culturing can be carried out in the following manner.

Any type of medium can be used, provided that a diglycosidase producing microorganism can be grown therein. For example, a medium to be used may contain carbon sources such as glucose, sucrose, gentiobiose, soluble starch, glycerol, dextrin, molasses and organic acids, nitrogen sources such as ammonium sulfate, ammonium carbonate, ammonium phosphate, ammonium acetate, peptone, yeast extract, corn steep liquor, casein hydrolysate, wheat bran and meat extract and inorganic salts such as potassium salts, magnesium salts, sodium salts, phosphates, manganese salts, iron salts and zinc salts. In addition, various inducers can be added to the medium in order to produce and accumulate diglycosidase. Examples of the inducers to be used include saccharides, preferably gentose (e.g., Gentose #80, Nihon Shokuhin Kako), gentiobiose and gentio-oligosaccharide (e.g., Gentio-oligosaccharide, Wako Pure Chemicals). Amount of these inducers to be added is not particularly limited, with the proviso that the amount is effective in increasing the productivity of diglycosidase to an intended level, but is added preferably in an amount of from 0.01 to 5%.

The medium pH is adjusted to a level of approximately from 3 to 8, preferably from about 5 to 6, and the culturing is carried out under aerobic conditions at a culturing temperature of generally from about 10 to 50° C., preferably at about 30° C., for a period of from 1 to 15 days, preferably from 4 to 7 days. Regarding the culturing method, shaking culture and aerobic submerged culture by a jar fermentor can be used. However, the aforementioned various culture conditions are optionally changed depending on the microorganisms or cells to be cultured as a matter of course, and such conditions are not particularly limited with the proviso that the diglycosidase of the present invention can be produced.

Regarding the isolation and purification of diglycosidase from the thus obtained culture broth, purified primeverosidase can be obtained in the usual way by a combination of centrifugation, UF concentration, salting out and various types of chromatography such as of an ion exchange resin.

The culture of the aforementioned microorganism as it is can be used as the enzyme composition of the present invention. Of course, the culture may be purified to an appropriate degree of purification depending on the intended use of the present invention.

The following further describes a gene which encodes a microorganism-derived enzyme of the present invention having the activity to act upon a disaccharide glycoside and thereby release saccharides from said disaccharide glycoside in disaccharide unit, a recombinant vector which contains said gene, a transformant into which said vector is introduced and a method for producing said enzyme using said transformant.

As the microorganism-derived enzyme of the present invention having the activity to act upon a disaccharide glycoside and thereby release saccharides from said disaccharide glycoside in disaccharide unit, all of the enzymes which can be obtained by the aforementioned production methods are included, in which particularly preferred one is a polypeptide which has the amino acid sequence of SEQ ID NO: 8 shown in the Sequence Listing, wherein one or more amino acid residues of the amino acid sequence may be modified by at least one of deletion, addition, insertion and substitution, and more preferred one is a polypeptide which has the amino acid sequence of SEQ ID NO: 8 shown in the Sequence Listing.

Examples of the gene which encodes the enzyme of the present invention include a gene which can be obtained from a microorganism capable of producing said enzyme by cloning of said gene and a gene which has a certain degree of homology with said gene. Regarding the homology, a gene having a homology of at least 50% or more, preferably a gene having a homology of 80% or more and more preferably a gene having a homology of 95% or more can be exemplified. The following polynucleotide (DNA or RNA) is desirable as the gene which encodes the enzyme of the present invention.

A polynucleotide which comprises a polynucleotide being selected from the following polynucleotides (a) to (g) and encoding a polypeptide having the activity to act upon a disaccharide glycoside and thereby release saccharides from said disaccharide glycoside in disaccharide unit;

(a) a polynucleotide which encodes a polypeptide having the amino acid sequence of SEQ ID NO: 8 shown in the Sequence Listing, (b) a polynucleotide which encodes a polypeptide having the amino acid sequence of SEQ ID NO: 8 shown in the Sequence Listing, wherein one or more amino acid residues of the amino acid sequence are modified by at least one of deletion, addition, insertion and substitution, (c) a polynucleotide which has the nucleotide sequence of SEQ ID NO: 7 shown in the Sequence Listing, (d) a polynucleotide which has the nucleotide sequence of SEQ ID NO: 7 shown in the Sequence Listing, wherein one or more bases of the nucleotide sequence are modified by at least one of deletion, addition, insertion and substitution, (e) a gene which hybridizes with any one of the aforementioned polynucleotides (a) to (d) under a stringent condition, (f) a polynucleotide which has homology with any one of the aforementioned polynucleotides (a) to (d), and (g) a polynucleotide which is degenerate with respect to any one of the aforementioned polynucleotides (a) to (f).

The gene which encodes the enzyme of the present invention can be prepared from the aforementioned microorganism capable of producing the enzyme of the present invention by carrying out cloning of said gene in the following manner. Firstly, the enzyme of the present invention is isolated and purified from a microorganism capable of producing the enzyme of the present invention by the aforementioned method and information on its partial amino acid sequence is obtained.

Regarding the determination method of a partial amino acid sequence, it is effective to carry out a method in which purified enzyme is directly applied to an amino acid sequence analyzer (such as Protein Sequenser 476A, manufactured by Applied Biosystems) by Edman degradation method [$J.$ $Biol.$ $Chem.$, vol. 256, pp. 7990–7997 (1981)], or a method in which limited hydrolysis of the enzyme is carried out using a protein hydrolase, the thus obtained peptide fragments are isolated and purified and then amino acid sequences of the thus purified peptide fragments are analyzed.

Based on the information of the thus obtained partial amino acid sequences, a gene which encodes the enzyme of the present invention is cloned. In general, the cloning is carried out making use of a PCR method or a hybridization method.

When a hybridization method is used, the method described in "Molecular Cloning, A Laboratory Manual" (edit. by T. Maniatis et al., Cold Spring Harbor Laboratory, 1989) may be used.

When a PCR method is used, the following method may be used.

Firstly, a gene fragment of interest is obtained by carrying out PCR reaction using genomic DNA of a microorganism capable of producing the enzyme of the present invention as the template and synthetic oligonucleotide primers designed based on the information of partial amino acid sequences. The PCR method is carried out in accordance with the method described in "PCR Technology" (edit. by Erlich H. A., Stockton Press, 1989). When nucleotide sequences of the thus amplified DNA fragments are determined by a usually used method such as the dideoxy chain termination method, a sequence which corresponds to the partial amino acid sequence of the enzyme of the present invention is found in the thus determined sequences, in addition to the sequences of synthetic oligonucleotide primers, so that a part of the enzyme gene of interest of the present invention can be obtained. As a matter of course, a gene which encodes complete enzyme of the present invention can be cloned by further carrying out a cloning method such as the hybridization method using the thus obtained gene fragment as a probe.

In the following Examples, a gene coding for the enzyme of the present invention was determined by the PCR method using $Aspergillus$ $fumigatus$ IAM 2046. Complete nucleotide sequence of the gene coding for the enzyme of the present invention originated from $Aspergillus$ $fumigatus$ is shown in the SEQ ID NO: 7, and the amino acid sequence encoded thereby was determined to be the sequence shown in the SEQ ID NO: 8. In this connection, there are countless nucleotide sequences which correspond to the amino acid sequence shown in the SEQ ID NO: 8, in addition to the nucleotide sequence shown in the SEQ ID NO: 8, and all of these sequences are included in the scope of the present invention.

The gene of interest can also be obtained by chemical synthesis based on the information of the amino acid sequence shown in the SEQ ID NO: 8 and the nucleotide sequence shown in the SEQ ID NO: 7 (cf. Gene, 60(1), 115–127 (1987)).

Regarding the gene of the object enzyme of the present invention, a polynucleotide which encodes a polypeptide having the amino acid sequence of SEQ ID NO: 8, wherein one or more amino acid residues of the amino acid sequence are modified by at least one of deletion, addition, insertion and substitution, a gene which hybridizes with said polynucleotide under a stringent condition, a polynucleotide which has homology with said polynucleotide and a polynucleotide which is degenerate with respect to said polynucleotide are also included in the present invention, with the proviso that the polypeptides encoded thereby have the enzyme activity of the present invention.

The term "under stringent condition" as used herein means, for example, the following condition. That is, 6×SSC, 1.0% blocking agent, 0.1% N-lauroylsarcosine sodium, 0.02% SDS.

By using the entire portion or a part of the enzyme gene of the present invention, whose complete nucleotide sequence has been revealed making use of *Aspergillus fumigatus* IAM2046, as a probe for hybridization, DNA fragments having high homology with the enzyme gene of the present invention shown in SEQ ID NO: 7 can be selected from genomic DNA libraries or cDNA libraries of microorganisms capable of producing other enzymes of the present invention.

The hybridization can be carried out under the aforementioned stringent condition. For example, DNAs from a genomic DNA library or a cDNA library obtained from a microorganism capable of producing an enzyme of the present invention is fixed on nylon membranes, and the thus prepared nylon membranes are subjected to blocking at 65° C. in a pre-hybridization solution containing 6×SSC, 0.5% SDS, 5× Denhart's and 100 µg/ml of salmon sperm DNA. Thereafter, each probe labeled with $^{32}$P or digoxigenin is added thereto, followed by incubation overnight at 68° C. The thus treated nylon membranes are washed in 6×SSC containing 0.1% SDS at room temperature for 10 minutes, in 6×SSC containing 0.1% SDS 45° C. for 30 minutes and then subsequently subjecting the thus washed membranes to an auto-radiography or detection of digoxigenin to detect a DNA fragment which hybridizes with the probe in a specific fashion. Also, genes which show various degree of homology can be obtained by changing certain conditions such as washing or lowering the hybridization temperature (e.g., 45° C.).

On the other hand, primers for use in the PCR reaction can be designed from the nucleotide sequence of the gene of the present invention. By carrying out the PCR reaction using these primers, gene fragments having high homology with the gene of the present invention can be detected and the complete gene can also be obtained.

In order to determine whether the thus obtained gene encodes a polypeptide having the enzyme activity of interest, the thus determined nucleotide sequence is compared with the nucleotide sequence coding for the enzyme of the present invention or with its amino acid sequence, and the identity is estimated based on the gene structure and homology. Alternatively, it is possible to determine whether the gene encodes a polypeptide which has the enzyme activity of interest by producing a polypeptide encoded by the gene and measuring its enzyme activity.

The following method is convenient for producing a polypeptide having the enzyme activity of the present invention using the enzyme gene of the present invention.

Firstly, transformation of a host is carried out using a vector containing the object gene of the enzyme of the present invention and then culturing of the thus obtained transformant is carried out under generally used conditions, thereby allowing the strain to produce a polypeptide having the enzyme activity of the present invention.

Examples of the host to be used include microorganisms, animal cells and plant cells. Examples of the microorganisms include bacteria such as *Escherichia coli* and other bacteria belonging to the genera *Bacillus, Streptomyces*, and *Lactococcus*, yeasts such as those belonging to the genera *Saccharomyces, Pichia* and *Kluyveromyces* and filamentous fungi such as those belonging to the genera *Aspergillus, Penicillium, Trichoderma* and *Rhizopus*. Examples of the animal cells include those which unitize the baculovirus expression system.

Confirmation of the expression and expressed product can be made easily by the use of an antibody specific for the enzyme of the present invention, and the expression can also be confirmed by measuring the enzyme activity of the present invention.

As described in the foregoing, purification of the enzyme of the present invention from the transformant culture medium can be carried out by optional combination of centrifugation, UF concentration, salting out and various types of chromatography such as of ion exchange resins.

In addition, since the primary structure and gene structure of the enzyme of the present invention have been revealed by the present invention, it is possible to obtain a gene coding for the amino acid sequence wherein one or more amino acid residues of the amino acid sequence are modified by at least one of deletion, addition, insertion and substitution, by introducing random mutation or site-specific mutation using the gene of the present invention. This method renders possible preparation of a gene coding for an enzyme of the present invention which has the enzyme activity of the present invention but its properties such as optimum temperature, temperature stability, optimum pH, pH stability and substrate specificity are slightly changed, and it also renders possible production of such enzymes of the present invention by means of genetic engineering techniques.

Examples of the method for introducing random mutation include a chemical DNA modification method in which a transition mutation is induced to convert cytosine base into uracil base by the action of sodium hydrogensulfite [*Proceedings of the National Academy of Sciences of the USA*, vol. 79, pp. 1408–1412 (1982)], a biochemical method in which base substitution is induced during the step of double strand formation in the presence of [α-S] dNTP [*Gene*, vol. 64, pp. 313–319 (1988)] and a PCR method in which PCR is carried out by adding manganese to the reaction system to decrease fidelity of the nucleotide incorporation [*Analytical Biochemistry*, vol. 224, pp. 347–353 (1995)].

Examples of the method for introducing site-specific mutation include a method in which amber mutation is employed [gapped duplex method; *Nucleic Acids Research*, vol. 12, no. 24, pp. 9441–9456 (1984)], a method in which recognition sites of restriction enzymes are used [*Analytical Biochemistry*, vol. 200, pp. 81-88 (1992); *Gene*, vol. 102, pp. 67–70 (1991)], a method in which mutation of dut (dUTPase) and ung (uracil DNA glycosylase) is used [Kunkel method; *Proceedings of the National Academy of Sciences of the USA*, vol. 82, pp. 488–492 (1985)], a method in which amber mutation is induced using DNA polymerase and DNA ligase [oligonucleotide-directed dual amber (ODA) method: *Gene*, vol. 152, pp. 271–275 (1995); JP-A-7-289262], a method in which a host introduced with a DNA repair system is used (JP-A-8-70874), a method in which a protein capable of catalyzing DNA chain exchange reaction is used (JP-A-8-140685), a method in which PCR is carried out using two different primers for mutation use to which recognition sites of restriction enzymes are added (U.S. Pat. No. 5,512,463), a method in which PCR is carried out using a double-stranded DNA vector having an inactivated drug resistance gene and two different primers [*Gene*, vol. 103, pp. 73–77 (1991)] and a method in which PCR is carried out making use of amber mutation (WO 98/02535).

Also, site-specific mutation can be introduced easily by the use of commercially available kits. Examples of such kits include MUTAN®-G Mutagenesis Kit (manufactured by Takara Shuzo) in which the gapped duplex method is used, MUTAN®-K Mutagenesis Kit (manufactured by Takara Shuzo) in which the Kunkel method is used, MUTAN®-Express Km Mutagenesis Kit (manufactured by Takara Shuzo) in which the ODA (Oligonucleotide-directed Dual Amber) method is used and QUICKCHANGE® Site-Directed Mutagenesis Kit (manufactured by STRAT-AGENE) in which primers for mutation use and *Pyrococcus furiosus* DNA polymerase are used, as well as TaKaRa BIOMEDICALS LA PCR in vitro Mutagenesis Kit (manufactured by Takara Shuzo) and MUTAN®-Super Express Km in vitro Mutagenesis Kit (manufactured by Takara Shuzo) (based on ODA method utilizing the advantage of LA (Long and Accurate) PCR technology) as kits in which PCR is used.

Thus, the primary structure and gene structure of the enzyme of the present invention provided by the present invention render possible production of an inexpensive and high purity polypeptide having the enzyme activity of the present invention by means of genetic engineering techniques.

In this connection, various literature and references are cited in the specification, and all of them are incorporated herein by references.

Next, various applications of the enzyme composition of the present invention are described.

Diglycosidase can be used for the improvement of various components such as aromas, colors and physiologically active contents of plant materials and for adjusting extraction efficiency of these components. In consequence, it can be used in the production of food and drinks having increased aromas and of spices, perfumes and liquid scents having increased aromas, and it also can be used for the early stage release of unfavorable odor by optionally using it during a step of the just described productions. Regarding the colors, it can be used for the improvement of hues of plant materials, food and drinks, development of colors and production of pigments.

In addition, similar to the case of aromatic components, it can be used for the degradation and removal of pigment precursors which are not desirable in view of qualities, and regarding the physiological activities, it can be used for the increase of pharmacological components and useful physiologically active components of crude drugs, herbs and other plant components or degradation and removal of undesirable components.

That is, it is possible to produce the aforementioned actions by allowing the diglycosidase of the present invention to act upon various disaccharide glycoside components.

In addition, the diglycosidase of the present invention may be administered with the aforementioned physiologically active substance, etc. after mixing or without mixing but by simultaneously or with a short interval administration, in order for the physiologically active substance to be absorbed efficiently into the body, etc.

Examples of the materials containing disaccharide glycosides to be treated by the present invention include those which undergo the action of diglycosidase, such as foods, cosmetics, medicaments, quasi drugs, agricultural chemicals and feeds, more illustratively, it can also be applied to the production of industrial products having various aromas, such as foods, toiletries, woodworks and mats produced from plant materials.

Food articles having aromatic components can be exemplified as materials to which the diglycosidase of the present invention is preferably applied. As illustrative examples, it can be used in the so-called "wilting" step during the production of oolong tea and jasmine tea and for the improvement of aromas of black tea (for tea pack by CTC method) and wine. It can also be used for the maintenance of aromas of cosmetics and liquid scents and improvement of aromas and pharmacological effects of medicaments.

The diglycosidase of the present invention is also useful in the production of pigments. For example, extraction of alizarine dye from *Rubia tinctorum* L. ruberythric acid can be carried out more efficiently than the conventional method by the use of the enzyme.

Also, it is possible to produce precursors of disaccharide components such as an aroma, a pigment, a physiologically active component and primeverose making use of the action of diglycosidase. Improvement of the stability and keeping quality of these components, their detoxication and modification of pharmacological components for DDS can be expected by their glycosylation.

In addition, diglycosidase can degrade modified glucosides such as acetylglucoside, malonylglucoside, methylglucoside, phosphoglucoside, and amidoglucoside which can hardly be utilized by glucosidase as its substrate more efficiently than known glucosidase. Making use of this property, absorption and yield of isoflavone contained in soybean can be improved by converting acetylglucoside and malonylglucoside of isoflavone into their aglycon forms.

The enzyme solution of the present invention may be sprayed to the cut flowers or may be abosorbed by the cut flowers to enhance the aroma of flowers.

Regarding application methods of diglycosidase, its adding method, adding amount, reaction method and the like can be changed at will depending on the conditions of material to be treated.

Regarding an illustrative application method, the diglycosidase of the present invention is added to a plant extract or fermentation product containing an aroma precursor, and the mixture is incubated. The reaction conditions are not particularly limited, with the proviso that the diglycosidase of the present invention can act upon the precursor of an aroma, pigment or physiologically active component to release the aroma, pigment or physiologically active component, and such conditions can be set by those skilled in the art without undue efforts. Under such conditions, concentration of said component can be increased.

Also, the enzyme of the present invention can be used for increasing concentration of an aroma, pigment or physiologically active component which is present in plants. That is, since plants contain precursors of these components, an aroma, pigment or physiologically active component in a plant can be increased by cultivating the plant with adding an effective amount of the diglycosidase of the present invention (including transgenic method) under such conditions that the precursor in said plant can be hydrolyzed. In addition, the formation period of an aroma, pigment or physiologically active component can be controlled making use of the enzyme composition of the present invention.

In this connection, it is possible to synthesize various types of glycoside by making use of reverse reaction of the diglycosidase of the invention.

BEST MODE FOR CARRYING OUT THE INVENTION

The invention is described further in detail in the following with reference to examples but, as a matter of course, the invention is not limited to the following examples without departing from its scope. Unless otherwise noted, the term % as used herein means w/v %.

EXAMPLE 1

Each of *Aspergillus niger* IFO 4407 and *Aspergillus niger* IAM 2020 was cultured overnight at 30° C. on a shaker in a pre-culture medium (composition; 0.2% yeast extract, 0.5% peptone, 2% glucose, 0.1% $KH_2PO_4$, 0.05% $MgSO_4 \cdot 7H_2O$, pH 5.7), the resulting culture broth in an amount of 1/100 was inoculated into a main culture medium (4% soybean flour, 0.3% sodium chloride, 0.1% $KH_2PO_4$, 0.05% $MgSO_4 \cdot 7H_2O$, 2% soluble starch, 1% red bran, pH 5.6), and cultured for 6 days on a shaker, and then the cells were removed from the culture broth to obtain a crude enzyme solution. Using this enzyme solution, diglycosidase activity and β-glucosidase activity were measured.

As the result, the diglycosidase activity and β-glucosidase activity in the strain IFO 4407 were 0.129 unit/ml and 4.34 units/ml, respectively, and the diglycosidase activity and β-glucosidase activity in the strain IAM 2020 were 0.156 unit/ml and 5.97 units/ml, respectively.

EXAMPLE 2

In accordance with Example 1, *Aspergillus fumigatus* IAM 2046 was pre-cultured in the same manner, and the resulting culture broth was inoculated into a main culture medium (2% soybean flour, 0.3% sodium chloride, 0.1% $KH_2PO_4$, 0.05% $MgSO_4 \cdot 7H_2O$, 3% soluble starch, 0.5% gentose #80 (mfd. by Nihon Shokuhin Kako), pH 5.6) and cultured for 4 days to obtain a crude enzyme solution. As the result, the diglycosidase activity was 0.106 unit/ml and β-glucosidase activity was 0.320 unit/ml.

EXAMPLE 3

Using *Aspergillus fumigatus* IAM 2046, effects of inducers on the production of diglycosidase were examined. *Aspergillus fumigatus* IAM 2046 was cultured for 6 days in a culture medium (2% soybean flour, 0.3% sodium chloride, 0.1% $KH_2PO_4$, 0.05% $MgSO_4 \cdot 7H_2O$, 3% soluble starch) supplemented with 0.1% of each of various saccharides, and the diglycosidase activity was measured. The results are shown in Table 3.

TABLE 3

| Inducers | Inducing ability (%) |
| --- | --- |
| Not added | 100 |
| Isomaltose | 145 |
| Maltotriose | 171 |
| Maltose | 136 |
| Gentose #80 | 235 |
| Gentiobiose | 211 |
| Gentio-oligosaccharide | 180 |
| Sucrose | 116 |
| Trehalose | 113 |
| Glucose | 164 |
| Galactose | 125 |
| Fructose | 143 |
| Rhamnose | 129 |
| Tulbose | 116 |
| Maltitol | 142 |
| Arabitol | 112 |
| Galactitol | 142 |
| Glucosamine hydrochloride | 157 |

As is evident from the above table, the producing ability of diglycosidase was increased by various saccharides. Particularly, markedly high inducing ability was found in gentose, gentiobiose and gentio-oligosaccharide.

In addition, similar effects were also found when *Aspergillus niger* IFO 4407 or *Aspergillus niger* IAM 2020 was used.

EXAMPLE 4

Each of the crude enzyme solutions obtained in Examples 1 and 2 was concentrated using an ultrafiltration membrane having a molecular weight cutoff of 6,000. Next, 1 ml of the concentrated solution was mixed with 1 ml of a 5 mg/ml pNP-primeveroside solution which had been prepared using 20 mM phosphate buffer (pH 6.0), and the mixture was incubated at 37° C. Samples were collected 1, 2, 4, 24 and 48 hours thereafter to confirm release of primeverose by a thin layer chromatography (TLC).

As a result, a spot was observed by TLC at the same position of a disaccharide primeverose in all of the culture media of two *Aspergillus niger* strains described in Example 1 and *Aspergillus fumigatus* described in Example 2. Such a spot was not observed in samples in which the crude enzyme concentration solutions were subjected to the same test after their heat treatment (100° C. for 10 minutes). Thus, the presence of an enzyme capable of releasing primeverose in disaccharide unit from pNP-primeveroside was found in the crude enzyme concentration solutions.

EXAMPLE 5

Screening of Diglycosidase in Various Microorganisms a) Preparation of Enzyme Samples Each microorganism to be subjected to screening was pre-cultured and main cultured. In the case of liquid culturing, the obtained culture broth was centrifuged at 10,000 $min^{-1}$ for 10 minutes and the resulting supernatant was used as the enzyme sample. In the case of solid culturing, the medium after completion of the culturing was extracted with water and the resulting extract was used as the enzyme sample.

In this connection, intracellular enzyme was also examined in the case of bacteria. In that case, the culture broth was centrifuged, and the thus obtained cells as the precipitate were washed with physiological saline, suspended in 10 times amount of 10 mM phosphate buffer (pH 7.0) based on the cell weight and then treated with ultrasonic wave to disrupt the cells. The disrupted suspension was centrifuged at 12,000 $min^{-1}$ for 20 minutes and the resulting supernatant was used as the intracellular enzyme sample.

Media and culture conditions regarding the culturing are shown in Tables 1 to 5.

TABLE 1

Liquid culturing of mold and yeast

Pre-culture: Medium composition

| | |
|---|---|
| Yeast extract (DIFCO) | 0.2% |
| Peptone (DIFCO) | 0.5% |
| Glucose (Katayama Chemical) | 2.0% |
| Potassium dihydrogenphosphate (Kanto Chemical) | 0.1% |
| Magnesium sulfate heptahydrate (Katayama Chemical) | 0.05% |

The above composition was dissolved in purified water and adjusted to pH 5.7 with 1 M hydrochloric acid and 1 M sodium hydroxide. The medium was dispensed in 100 ml portions into Sakaguchi flasks and then sterilized at 121° C. for 20 minutes under 1 atmospheric pressure.

Pre-Culture: Culture Conditions

The culturing was carried out at a shaking speed of 140 min$^{-1}$, with one loopful inoculum from a slant culture, for 1 day or more and at 30° C. Regarding yeast strains, temperature condition was set to 25° C.

| Main culture: Medium composition | |
|---|---|
| Soya flower A (Nisshin) | 2.0% |
| Sodium chloride (Kanto Chemical) | 0.3% |
| Dipotassium hydrogenphosphate (Kanto Chemical) | 0.1% |
| Magnesium sulfate heptahydrate (Katayama Chemical) | 0.05% |
| Soluble starch (Wako Pure Chemical) | 3.0% |
| Gentose #80 (Nihon Shokuhin Kako) | 0.5% |

The above composition was dissolved in purified water and adjusted to pH 5.6 with 1 M hydrochloric acid and 1 M sodium hydroxide. The medium was dispensed in 100 ml portions into Sakaguchi flasks and then sterilized at 121° C. for 20 minutes under 1 atmospheric pressure.

The culturing was carried out using the medium both in the presence and absence of gentose #80.

Main Culture: Culture Conditions

The culturing was carried out at a shaking speed of 140 min$^{-1}$, with 1 ml inoculum from the pre-culture broth, for 5 days and at 30° C. Regarding yeast strains, the temperature condition was set to 25° C.

TABLE 2

Solid culturing of mold and yeast

Pre-culture: Medium composition

| | |
|---|---|
| High starch bran (B Ohgi, Nippon Flower Milling) | 8.3% |

The above composition was suspended in purified water, and the medium was dispensed in 9 ml portions into culture test tubes and then sterilized at 121° C. for 20 minutes under one atmospheric pressure.

Pre-Culture: Culture Conditions

The culturing was carried out at a shaking speed of 300 min$^{-1}$, with one loopful inoculum from a slant culture, for 1 to 2 days and at 30° C.

Main Culture: Medium Composition

A 5.0 g portion of bran was suspended in 1.5 ml of purified water, dispensed into 100 ml capacity conical flasks and then sterilized at 121° C. for 20 minutes under one atmospheric pressure.

Main Culture: Culture Conditions

The culturing was carried out with 1 ml inoculum from the pre-culture broth, for 3 days and at 30° C.

Extraction

By adding 90 ml of tap water, extracted overnight at 8° C. or below.

TABLE 3

Culturing of bacteria and actinomycetes

Pre-culture: Medium composition
Tryptic soy broth (DIFCO)

| | | |
|---|---|---|
| BACTO Tryptone | 1.7% | |
| BACTO Soytone | 0.3% | |
| BACTO Dextrose | 0.2% | pH 7.3 ± 0.2 |
| Sodium chloride | 0.5% | |
| Dipotassium hydrogenphosphate | 0.25% | |

The above composition was dissolved in purified water, and the medium was dispensed in 100 ml portions into Sakaguchi flasks and then sterilized at 121° C. for 20 minutes under one atmospheric pressure.

Pre-Culture: Culture Conditions

The culturing was carried out at a shaking speed of 140 min$^{-1}$, with one loopful inoculum from a slant culture, for 1 day or more and at 30° C.

| Main culture: Medium composition | |
|---|---|
| Polypeptone (Japan Pharmaceutical) | 1.0% |
| Yeast extract (DIFCO) | 0.25% |
| Ammonium sulfate (Wako Pure Chemical) | 0.1% |
| Dipotassium hydrogenphosphate (Kanto Chemical) | 0.05% |
| Magnesium sulfate heptahydrate (Katayama Chemical) | 0.025% |
| Calcium chloride (Wako Pure Chemical) | 0.0001% |
| Adekanol LG126 (Asahi Denka) | 0.001% |
| Gentose #80 (Nihon Shokuhin Kako) | 0.5% |

The above composition was dissolved in purified water and adjusted to pH 7.0 with 1 M hydrochloric acid and 1 M sodium hydroxide. The medium was dispensed in 100 ml portions into Sakaguchi flasks and then sterilized at 121° C. for 20 minutes under one atmospheric pressure.

The culturing was carried out using the medium both in the presence and absence of gentose #80.

Main Culture: Culture Conditions

The culturing was carried out at a shaking speed of 140 min$^{-1}$, with 1 ml inoculum from the pre-culture broth, for 5 days and at 30° C.

TABLE 4

Culturing of Penicillium multicolor

Pre-culture: Medium composition

| | |
|---|---|
| Defatted soybean "Soypro" (Hohnen Oil) | 2.0% |
| Glucose (Katayama Chemical) | 3.0% |
| Potassium dihydrogenphosphate (Kanto Chemical) | 0.5% |
| Ammonium sulfate (Wako Pure Chemical) | 0.4% |

TABLE 4-continued

Culturing of Penicillium multicolor

Pre-culture: Medium composition

| | |
|---|---|
| Dry yeast | 0.3% |
| Adekanol (Asahi Denka) | 0.05% |

The above composition was dissolved in purified water, and the medium was dispensed in 100 ml portions into Sakaguchi flasks and then sterilized at 121° C. for 20 minutes under one atmospheric pressure.

Pre-Culture: Culture Conditions

The culturing was carried out at a shaking speed of 140 min$^{-1}$, with one loopful inoculum from a slant culture, for 5 days or more and at 27° C.

| Main culture: Medium composition | |
|---|---|
| Gentose #80 (Nihon Shokuhin Kako) | 3.0% |
| Potassium dihydrogenphosphate (Kanto Chemical) | 2.0% |
| Ammonium sulfate (Wako Pure Chemical) | 1.0% |
| Meast P1G (Asahi Beer Food) | 3.13% |
| Adekanol LG126 (Asahi Denka) | 0.05% |

The above composition was dissolved in purified water, and the medium was dispensed in 100 ml portions into Sakaguchi flasks and then sterilized at 121° C. for 20 minutes under one atmospheric pressure.

Main Culture: Culture Conditions

The culturing was carried out at a shaking speed of 140 min$^{-1}$, with 1 ml inoculum from the pre-culture broth, for 6 days and at 27° C.

TABLE 5

Culturing of the genus Corynebacterium

Pre-culture: Medium composition

| | |
|---|---|
| Glucose | 0.2% |
| Yeast extract | 0.1% |
| Ammonium nitrate | 0.4% |
| Potassium dihydrogenphosphate | 0.15% |
| Sodium hydrogenphosphate dodecahydrate | 0.15% |
| Magnesium sulfate heptahydrate | 0.02% |
| Ferrous sulfate heptahydrate | 0.0001% |
| Calcium chloride dihydrate | 0.001% |

The above composition was dissolved in purified water and adjusted to pH 7.0 with 1 M hydrochloric acid and 1 M sodium hydroxide. The medium was dispensed in 10 ml portions into culture test tubes and then sterilized at 121° C. for 20 minutes under one atmospheric pressure.

Pre-Culture: Culture Conditions

The culturing was carried out at a shaking speed of 300 min$^{-1}$, with one loopful inoculum from a slant culture, for 2 days and at 30° C.

| Main culture: Medium composition | |
|---|---|
| Eugenyl-β-primeveroside | 0.2% |
| Yeast extract | 0.1% |
| Ammonium nitrate | 0.4% |
| Potassium dihydrogenphosphate | 0.15% |
| Sodium hydrogenphosphate dodecahydrate | 0.15% |
| Magnesium sulfate heptahydrate | 0.02% |
| Ferrous sulfate heptahydrate | 0.0001% |
| Calcium chloride dihydrate | 0.001% |

The above composition was dissolved in purified water and adjusted to pH 7.0 with 1 M hydrochloric acid and 1 M sodium hydroxide. The medium was dispensed in 10 ml portions into culture test tubes and then sterilized at 121° C. for 20 minutes under one atmospheric pressure.

Main Culture: Culture Conditions

The culturing was carried out at a shaking speed of 140 min$^{-1}$, with 1 ml inoculum from the pre-culture broth, for 1 day and at 30° C.

b) Preparation of Substrate Solution pNP-β-primeveroside was dissolved in 20 mM acetate buffer (pH 5.5) to a concentration of 5 mg/ml and used as a substrate solution A. Eugenyl-β-primeveroside was dissolved in 20 mM acetate buffer (pH 5.5) to a concentration of 10 mg/ml and used as a substrate solution B.

c) Enzyme Reaction

A 100 µl portion of the substrate solution A was put into a micro-centrifugation tube and mixed with 100 µl of each enzyme sample to carry out 96 hours of the enzyme reaction in a water bath of 37° C. When the reaction reached the intended time, the reaction solution was treated at 100° C. for 10 minutes to stop the enzyme reaction. This was used as the enzyme reaction-completed solution.

As a comparative control of the enzyme sample, the same enzyme sample was treated at 100° C. for 10 minutes before the enzyme reaction and subjected to the same reaction. The enzyme reaction was carried out on each of the substrate solutions A and B. When the substrate solution B was used, the reaction was carried out in the same manner as the case of the substrate solution A.

d) Thin Layer Chromatography

20 µl of the enzyme reaction-completed solution was spotted on a thin layer of silica gel (Silica gel 60 F254 [1.05554], Merck) and dried. This was developed twice with a developing solvent prepared by mixing ethyl acetate, acetic acid and purified water at a ratio of 3:1:1. After completion of the development, the thin layer was air-dried. Thereafter, a color developing reagent prepared by mixing sulfuric acid and methanol at a ratio of 20:80 was sprayed all over the thin layer after completion of the development, and the color was developed at 105° C. for about 10 minutes.

An enzyme sample by which the spot of primeverose was appeared on the thin layer after the color development was judged that the primeverosidase was present therein, and this producer strain was judged as a diglycosidase producing strain.

e) Results of the Screening of Diglycosidase Producing Strains

A summary of the diglycosidase producing strains found by the above evaluation method is shown in Table 6.

TABLE 6

Strains in which the diglycosidase production was found

| Microorganisms | Strain names |
| --- | --- |
| Mold | *Aspergillus oryzae* IAM 2769 |
| | *Aspergillus niger* |
| | IAM 2020 |
| | IFO 4091 |
| | IFO 9455 |
| | IAM 2107 |
| | *Aspergillus aculeatus* |
| | *Penicillium rugolosum* IFO 7242 |
| | *Penicillium lilacinum* IFO 5350 |
| | *Penicillium decumbence* IFO 31297 |
| | *Penicillium multicolor* IAM 7153 |
| | *Rhizopus oryzae* JCM 5560 |
| | *Rhizomucor pusillus* IAM 6122 |
| | *Rhizomucor miehei* IFO 9740 |
| | *Talaromyces emersonii* IFO 9747 |
| | *Mortierella vinacea* IFO 7875 |
| Yeast | *Cryptococcus albidus* IAM 12205 |
| Bacteria | *Microbacterium arborescens* JCM 5884 |
| | *Corynebacterium ammoniagenes* IFO 12072 |
| | *Corynebacterium ammoniagenes* IFO 12612 |
| | *Corynebacterium glutamicum* IFO 1318 |
| Actinomycetes | *Actinoplanes missouriensis* JCM 3121 |

EXAMPLE 6

Purification of Diglycosidase Derived from *Aspergillus fumigatus*

As the pre-culture, *Aspergillus fumigatus* IAM 2046 was inoculated into a glucose-peptone medium (0.2% yeast extract, 0.5% peptone, 2% glucose, 0.1% potassium dihydrogenphosphate, 0.05% magnesium sulfate, pH 5.7) and cultured at 30° C. for 24 hours on a shaker. The pre-culture broth was inoculated in an inoculum size of 1% into the main culture medium (2% Soya flower, 0.3% sodium chloride, 0.1% dipotassium hydrogenphosphate, 0.05% magnesium sulfate, 3% soluble starch, 1% gentose #80, pH 5.6) and cultured at 30° C. for 6 days on a shaker.

Cells were removed from the culture broth by filter paper filtration, and 8,600 ml of the resulting filtrate was concentrated to 710 ml using an ultrafiltration membrane of 6,000 molecular weight cutoff (AIP-1010, mfd. by Asahi Chemical Industry). A 200 ml portion of the concentrated solution was centrifuged at 4° C. and at 15,000 rpm for 10 minutes, and 192 ml of the supernatant was mixed with 55.9 g of ammonium sulfate (50% saturation) and stirred overnight at 4° C. This was centrifuged at 4° C. and at 15,000 rpm for 10 minutes, and the thus obtained precipitate was dissolved in 10 ml of 20% saturation ammonium sulfate/20 mM phosphate buffer (pH 6.0) and centrifuged at 4° C. and at 15,000 rpm for 10 minutes to recover the supernatant. A 9.5 ml portion of the supernatant was applied to a Phenyl Sepharose column (16×100 mm, mfd. by Pharmacia) which had been equilibrated with 20% saturation ammonium sulfate/20 mM phosphate buffer (pH 6.0), and the adsorbed protein was released by an ammonium sulfate linear density gradient of from 20% to 0%. The active peaks were recovered, buffer-exchanged to 25 mM triethanolamine buffer (pH 8.3) using 10DG column (mfd. by BIO-RAD), applied to an anion exchange Mono-P column (5×200 mm, mfd. by Pharmacia) which had been equilibrated with 25 mM triethanolamine buffer (pH 8.3) and then eluted with Polybuffer (pH 5.0, mfd. by Pharmacia), and the thus adsorbed protein was released by a pH linear density gradient of from pH 8.3 to pH 5.0 to obtain a purified enzyme preparation of diglycosidase. An SDS-PAGE analysis confirmed that the enzyme was purified as a single band of 47 kDa. Also, when it was treated with Endoglycosidase H (mfd. by BOEHRINGER MANNHEIM), changes in the band size were not found.

EXAMPLE 7

Physicochemical Properties of Diglycosidase Derived from *Aspergillus fumigatus*

Its optimum pH was measured in the following manner. A 400 μl portion of 2 mM pNP-primeveroside solution which had been adjusted to a respective pH value of from pH 2 to 5 with 20 mM secondary citric acid-HCl buffer was incubated at 37° C. for 5 minutes. Next, this was mixed with 90 μl of the enzyme solution to carry out the reaction at 37° C. for 20 minutes. The reaction was stopped by adding 500 μl of 0.5 M sodium carbonate solution, and the activity measurement was carried out by measuring the absorbance at 420 nm. As a result, it was found that its optimum pH was from 2.5 to 3.0. It was found that it shows sufficient activity at pH 3 which is more lower pH value than those of plant-derived enzymes having similar activity.

Its optimum temperature was measured in the following manner. A 400 μl portion of 2 mM pNP-primeveroside solution prepared using 20 mM disodium citric acid-HCl buffer (pH 2.5) was mixed with 90 μl of the enzyme solution to carry out the reaction at 30 to 65° C. for 20 minutes. The reaction was stopped by adding 500 μl of 0.5 M sodium carbonate solution, and the activity was determined by measuring the absorbance at 420 nm. It was found that sufficient activity is maintained, because diglycosidase derived from *Aspergillus fumigatus* has 80% of the activity even at 60° C., in comparison with the plant-derived enzymes having similar activity.

Its pH stability was measured in the following manner. The purified enzyme preparation was diluted 100 times with each of disodium citrate buffer of from pH 2 to 5, phosphate buffer of from pH 6 to 8 or glycine NaCl—NaOH buffer of from pH 7 to 10 and treated at 37° C. for 1 hour, and then a 90 μl portion thereof was mixed with 400 μl of 2 mM pNP-primeveroside solution (pH 2.5) which had been incubated at 37° C. for 5 minutes, and the reaction was carried out at 37° C. for 20 minutes. The reaction was stopped by adding 500 μl of 0.5 M sodium carbonate solution, and the activity measurement was carried out by measuring the absorbance at 420 nm to calculate the residual activity. As a result, its pH stability was 100% at pH 8 and it was stable within a range of from pH 3 to 8. It was found that this enzyme is stable within broader pH range in comparison with plant-derived enzymes which have similar activity and are stable at pH 4 to 7.

Thermal stability of the purified preparation was examined by diluting it 100 times with 20 mM glycine NaCl—NaOH buffer (pH 8), treating the dilution at each temperature of from 30 to 55° C. for 1 hour and then measuring the residual activity. As a result, the activity was stable at a temperature of 50° C. or below. It was found that this enzyme was stable broader range of temperature, in comparison with plant-derived enzymes which have similar activity and are stable at 45° C. or below.

Physicochemical Properties of Diglycosidase Derived from Other Microorganisms

Diglycosidase samples, the production of which had been confirmed by the same method as described in Example 5, were examined for physicochemical properties. As a result, it was found that diglycosidase has an activity enough for practical use at pH 3 or less because of its optimum pH ranging from 3 to 6, that it has an activity enough for practical use at 50° C. or more because of its optimum temperature ranging from 30° C. to 60° C., and that it is stable at pH 3 to 8 and at 50° C. or less. Thus, diglycosidase derived from microorganisms can be used in relatively broad ranges of pH and temperature in comparison with similar enzymes derived from plants and is superior thereto in stability.

EXAMPLE 8

Isolation of Gene Coding for the Diglycosidase Derived from *Aspergillus fumigatus*

Unless otherwise noted, gene manipulation techniques employed herein were carried out in accordance with a textbook (e.g., Molecular Cloning 2nd ed., Cold Spring Harbor Laboratory Press, 1989).

a) Isolation of Chromosomal DNA

*Aspergillus fumigatus* IAM 2046 was inoculated into a glucose-peptone medium (0.2% yeast extract, 0.5% peptone, 2% glucose, 0.1% potassium dihydrogenphosphate, 0.05% magnesium sulfate, pH 5.7) and cultured at 30° C. for 3 days on a shaker.

In accordance with the method of Michael J. Hynes (*Molecular and Cellular Biology*, 1983, Vol. 3, No. 8, 1430–1439), 0.2 ml of chromosomal DNA having a concentration of 12.6 mg/ml was obtained from 300 ml of the culture broth.

b) Determination of Partial Amino Acid Sequence

The purified enzyme preparation of diglycosidase obtained in the Example was applied to a protein sequencer (mfd. by Hewlett Packard) to determine the 22 residue N-terminal amino acid sequence shown in SEQ ID NO: 1. Next, the purified enzyme preparation of diglycosidase obtained in the Example was subjected to reductive carboxylmethylation and then digested with lysyl endopeptidase. The thus obtained digest was applied to a reverse phase liquid chromatography, and one of the digested peptide fractions was applied to the protein sequencer to determine the 22 residue internal amino acid sequence shown in SEQ ID NO: 2.

SEQ ID NO: 1

Ala-Ala-Ser-Ala-Ser-Ala-Tyr-Cys-Ser-Asn-Ser-Ala-Gly-Asn-Tyr-Lys-Leu-Ser-Ser-Ile-Ala-Ala

SEQ ID NO: 2

Leu-Met-Thr-Pro-Ala-Gly-Ala-Asn-Phe-Ala-Leu-Met-Arg-His-Thr-Ile-Gly-Ala-Ser-Asp-Leu-Ser c) Preparation of DNA Probe by PCR Based on the N-terminal amino acid sequence and internal amino acid sequence, the following four mixed oligonucleotides were synthesized by a DNA synthesizer and used as PCR primers.

SEQ ID NO: 3

Sense primer:

5'-ACGAATTCAA(TC)(TA)(CG)IGC(TCAG)GGIAA(TC)TA(TC)AA-3'

SEQ ID NO: 4

Sense primer:

5'-CGGAATTCTA(TC)TG(TC)(TA)(CG)IAA(TC)(TA)(CG)IGC(TCAG)GG-3'

SEQ ID NO: 5

Antisense primer:

5'-TCAAGCTTGC(AG)AA(AG)TTIGC(TCAG)CCIGC(TCAG)GG-3'

SEQ ID NO: 6

Antisense primer:

5'-AGAAGCTTGCICC(TAG)ATIGT(AG)TG(TCAG)C(TG)CAT

Using these primers and the *Aspergillus fumigatus* chromosomal DNA as the template, PCR reaction was carried out under the following conditions using GeneAmp PCR System 9600 (Perkin Elmer).

| <PCR reaction solution> | |
| --- | --- |
| 10 x PCR reaction buffer (Perkin Elmer) | 10 μl |
| dNTP mixed solution (each 2 mM, Perkin Elmer) | 10 μl |
| 25 mM MgCl₂ (Perkin Elmer) | 6 μl |
| chromosomal DNA solution (100 μg/ml) | 1 μl |
| 40 μM sense primer | 2.5 μl |
| 40 μM antisense primer | 2.5 μl |
| sterilized water | 67.5 μl |
| Amplitaq Gold (5 U/μl, Perkin Elmer) | 0.5 μl |

| <PCR reaction conditions> | | |
| --- | --- | --- |
| Stage 1: | denaturation (95° C., 9 minutes) | 1 cycle |
| Stage 2: | denaturation (94° C., 45 seconds) annealing (55° C., 1 minute) elongation (72° C., 2 minutes) | 30 cycles |
| Stage 3: | elongation (72° C., 10 minutes) | 1 cycle |

When the thus obtained DNA fragment of about 0.27 kbp was cloned into pUC19 (TOYOBO) and then its nucleotide sequence was examined, a nucleotide sequence coding for the partial amino acid sequence described in the foregoing was found between just after the sense primer and just before the antisense primer. This DNA fragment was used as the DNA probe for the gene cloning.

d) Preparation of Gene Library

By recovering total RNA from *Aspergillus fumigatus*, Poly(A) RNA was prepared using Poly(A)Quick mRNA Isolation Kit (mfd. by STRATAGENE). Next, cDNA was synthesized using ZAP-cDNA Synthesis Kit (mfd. by STRATAGENE), ligated to λZAP II vector (mfd. by STRATAGENE) and then subjected to packaging using Gigapack III Gold (mfd. by STRATAGENE) to obtain a gene library.

e) Screening of Gene Library

The 0.27 kbp DNA fragment obtained in the aforementioned step c) was labeled using DIG-High Prime (mfd. by BOEHRINGER MANNHEIM). Using this as the DNA probe, the gene library obtained in the step d) was screened by plaque hybridization. After recovering phage particles from the thus obtained positive plaques, a plasmid pAFPri containing a cDNA of about 1.7 kbp was obtained by the in vivo excision method in accordance with the instruction of STRATAGENE.

f) Determination of Nucleotide Sequence

A nucleotide sequence coding for the diglycosidase is shown in SEQ ID NO: 7. Also, an amino acid sequence encoded by the SEQ ID NO: 7 is shown in SEQ ID NO: 8. Since the N-terminal amino acid sequence (SEQ ID NO: 1) and internal amino acid sequence (SEQ ID NO: 2) determined in the step b) were found in this amino acid sequence, it was confirmed that this DNA fragment is a diglycosidase gene fragment.

```
SEQ ID NO: 7 gccgcctctg cttcggctta ctgttccaac tcggccggca actacaagct gtcctccatc    60
gcagctccgg ttcaaggggc cggaaacccc ggctcggaat cgacctggca attgaccgtt   120
gacgacactt cgtccggtca caaacagacg atagttgggt tcggtgctgc tgtcactgat   180
gccacggtca cctcgttcaa cactttgtcc gcctccgtgc tgcaagactt gctcaataaa   240
ctgatgacac ctgccggggc gaactttgct tgatgcgac atactattgg ggcttcggat   300
ctgtccggtg acccagccta cacgtacgat gacaatggtg ggaaagcgga tccgtcactg   360
tcgggattca acctggggga ccgcggaacg gctatggcca agatgttggc aacaatgaag   420
tctctgcagc ccaacctcaa gatcctcggc tctccctgga gtgcaccagg atggatgaag   480
ctgaacgggg tccttgatgg caatacgaac aacaacaact gaacgatgg atacctaacc   540 agtgggggaa ccggtagtac ggggtatgcc agtcaattcg cgcagtactt tgtcaagtac   600
attcaggcct ataagaatct cggtgctcac gtcgacgcga ttaccatcca gaacgagccg   660
ctgttcagct cagcgggcta tcccaccatg tatgtctacg attatgagtc ggcacagctg   720
atccagaact acatcggccc cgctcttgcc agcgcggggc tagatacgga aatctgggct   780
tatgaccaca acacagatgt cccgtcgtac ccccagactg tccttaacca ggccggtcag   840
tacgtcaagt cggtggcctg gcactgctac gctcccaacg tcgactggac cgtgctcagc   900
cagttccaca acacaaaccc tggagtgaag caatatatga ccgagtgctg gactccagca   960
tctggcgcat ggcatcaggc ggcggacttc accatgggtc ccctgcagaa ctgggcctcg  1020
ggagtggcag catggactct gggaaccaac gctcaggatg gtccgcatct gtccactggc  1080
ggctgcgcga catgtcaagg cttggtgacc atcaacaacg gaggatacac gctcaacacc  1140
gcatactaca tgatggcgca attcagcaag ttcatgccgc tggtgcgat tgtgctcaat  1200 ggcagtggca gctacacgta ctctggcgga ggcggtatcc agtccgtggc ttccttgaat  1260
cccgatggaa cccgcactgt ggttattgaa aacacttttg caatgatgt ctatgtgact  1320 gtcactatga agagcgggca gaagtggagt gggaacgccc ctagccaatc cgtgactacc  1380
tgggttcttc catctgcttg a                                            1401

SEQ ID NO: 8

Ala Ala Ser Ala Ser Ala Tyr Cys Ser Asn Ser Ala Gly Asn Tyr Lys
 1               5                  10                  15

Leu Ser Ser Ile Ala Ala Pro Val Gln Gly Ala Gly Asn Pro Gly Ser
             20                  25                  30

Glu Ser Thr Trp Gln Leu Thr Val Asp Asp Thr Ser Ser Gly His Lys
         35                  40                  45

Gln Thr Ile Val Gly Phe Gly Ala Ala Val Thr Asp Ala Thr Val Thr
     50                  55                  60

Ser Phe Asn Thr Leu Ser Ala Ser Val Leu Gln Asp Leu Leu Asn Lys
 65                  70                  75                  80

Leu Met Thr Pro Ala Gly Ala Asn Phe Ala Leu Met Arg His Thr Ile
             85                  90                  95

Gly Ala Ser Asp Leu Ser Gly Asp Pro Ala Tyr Thr Tyr Asp Asp Asn
            100                 105                 110
```

-continued

```
Gly Gly Lys Ala Asp Pro Ser Leu Ser Gly Phe Asn Leu Gly Asp Arg
        115                 120                 125
Gly Thr Ala Met Ala Lys Met Leu Ala Thr Met Lys Ser Leu Gln Pro
    130                 135                 140
Asn Leu Lys Ile Leu Gly Ser Pro Trp Ser Ala Pro Gly Trp Met Lys
145                 150                 155                 160
Leu Asn Gly Val Leu Asp Gly Asn Thr Asn Asn Asn Leu Asn Asp
                165                 170                 175
Gly Tyr Leu Thr Ser Gly Gly Thr Gly Ser Thr Gly Tyr Ala Ser Gln
            180                 185                 190
Phe Ala Gln Tyr Phe Val Lys Tyr Ile Gln Ala Tyr Lys Asn Leu Gly
    195                 200                 205
Ala His Val Asp Ala Ile Thr Ile Gln Asn Glu Pro Leu Phe Ser Ser
    210                 215                 220
Ala Gly Tyr Pro Thr Met Tyr Val Tyr Asp Tyr Glu Ser Ala Gln Leu
225                 230                 235                 240
Ile Gln Asn Tyr Ile Gly Pro Ala Leu Ala Ser Ala Gly Leu Asp Thr
                245                 250                 255
Glu Ile Trp Ala Tyr Asp His Asn Thr Asp Val Pro Ser Tyr Pro Gln
            260                 265                 270
Thr Val Leu Asn Gln Ala Gly Gln Tyr Val Lys Ser Val Ala Trp His
    275                 280                 285
Cys Tyr Ala Pro Asn Val Asp Trp Thr Val Leu Ser Gln Phe His Asn
    290                 295                 300
Thr Asn Pro Gly Val Lys Gln Tyr Met Thr Glu Cys Trp Thr Pro Ala
305                 310                 315                 320
Ser Gly Ala Trp His Gln Ala Ala Asp Phe Thr Met Gly Pro Leu Gln
                325                 330                 335
Asn Trp Ala Ser Gly Val Ala Ala Trp Thr Leu Gly Thr Asn Ala Gln
            340                 345                 350
Asp Gly Pro His Leu Ser Thr Gly Gly Cys Ala Thr Cys Gln Gly Leu
    355                 360                 365
Val Thr Ile Asn Asn Gly Gly Tyr Thr Leu Asn Thr Ala Tyr Tyr Met
    370                 375                 380
Met Ala Gln Phe Ser Lys Phe Met Pro Pro Gly Ala Ile Val Leu Asn
385                 390                 395                 400
Gly Ser Gly Ser Tyr Thr Tyr Ser Gly Gly Gly Ile Gln Ser Val
                405                 410                 415
Ala Ser Leu Asn Pro Asp Gly Thr Arg Thr Val Val Ile Glu Asn Thr
            420                 425                 430
Phe Gly Asn Asp Val Tyr Val Thr Val Thr Met Lys Ser Gly Gln Lys
    435                 440                 445
Trp Ser Gly Asn Ala Pro Ser Gln Ser Val Thr Thr Trp Val Leu Pro
    450                 455                 460
Ser Ala
465
```

The open reading frame of this gene is shown in SEQ ID NO: 9. As shown in SEQ ID NO: 10, the entire portion is coded as a preprotein of 488 amino acids, of which the N-terminal 22 residues are assumed to be the pre-region and the remaining 466 residues correspond to the mature protein (cf. SEQ ID NO: 8).

The invention is not only particularly limited to a polypeptide having an activity to act upon a disaccharide glycoside to release saccharides from the disaccharide glycoside in disaccharide unit and a nucleotide which encodes the same, but also includes a more longer polypeptide comprising the former polypeptide (e.g., precursor) and a nucleotide which encodes the same.

SEQ ID NO: 9

```
ggcgacacca gaaagcaacc aagagcacga cacggactta ttctctttg aca atg    56
                                                          Met cgt ata tct gtc ggt gct ctg ctt ggc ttg aca gcc ctg agt cat gcc  104
Arg Ile Ser Val Gly Ala Leu Leu Gly Leu Thr Ala Leu Ser His Ala
    -20             -15                 -10 aca aca gag aaa cga gcc gcc tct gct tcg gct tac tgt tcc aac tcg  152
Thr Thr Glu Lys Arg Ala Ala Ser Ala Ser Ala Tyr Cys Ser Asn Ser
 -5              -1  1               5                      10 gcc ggc aac tac aag ctg tcc tcc atc gca gct ccg gtt caa ggg gcc  200
Ala Gly Asn Tyr Lys Leu Ser Ser Ile Ala Ala Pro Val Gln Gly Ala
             15                  20                  25 gga aac ccc ggc tcg gaa tcg acc tgg caa ttg acc gtt gac gac act  248
Gly Asn Pro Gly Ser Glu Ser Thr Trp Gln Leu Thr Val Asp Asp Thr
         30                  35                  40 tcg tcc ggt cac aaa cag acg ata gtt ggg ttc ggt gct gct gtc act  296
Ser Ser Gly His Lys Gln Thr Ile Val Gly Phe Gly Ala Ala Val Thr
     45                  50                  55 gat gcc acg gtc acc tcg ttc aac act ttg tcc gcc tcc gtg ctg caa  344
Asp Ala Thr Val Thr Ser Phe Asn Thr Leu Ser Ala Ser Val Leu Gln
 60                  65                  70                  75 gac ttg ctc aat aaa ctg atg aca cct gcc ggg gcg aac ttt gct ttg  392
Asp Leu Leu Asn Lys Leu Met Thr Pro Ala Gly Ala Asn Phe Ala Leu
             80                  85                  90 atg cga cat act att ggg gct tcg gat ctg tcc ggt gac cca gcc tac  440
Met Arg His Thr Ile Gly Ala Ser Asp Leu Ser Gly Asp Pro Ala Tyr
         95                 100                 105 acg tac gat gac aat ggt ggg aaa gcg gat ccg tca ctg tcg gga ttc  488
Thr Tyr Asp Asp Asn Gly Gly Lys Ala Asp Pro Ser Leu Ser Gly Phe
     110                 115                 120 aac ctg ggg gac cgc gga acg gct atg gcc aag atg ttg gca aca atg  536
Asn Leu Gly Asp Arg Gly Thr Ala Met Ala Lys Met Leu Ala Thr Met
 125                 130                 135 aag tct ctg cag ccc aac ctc aag atc ctc ggc tct ccc tgg agt gca  584
Lys Ser Leu Gln Pro Asn Leu Lys Ile Leu Gly Ser Pro Trp Ser Ala
140                 145                 150                 155 cca gga tgg atg aag ctg aac ggg gtc ctt gat ggc aat acg aac aac  632
Pro Gly Trp Met Lys Leu Asn Gly Val Leu Asp Gly Asn Thr Asn Asn
             160                 165                 170 aac aac ttg aac gat gga tac cta acc agt ggg ggg acc ggt agt acg  680
Asn Asn Leu Asn Asp Gly Tyr Leu Thr Ser Gly Gly Thr Gly Ser Thr
         175                 180                 185 ggg tat gcc agt caa ttc gcg cag tac ttt gtc aag tac att cag gcc  728
Gly Tyr Ala Ser Gln Phe Ala Gln Tyr Phe Val Lys Tyr Ile Gln Ala
     190                 195                 200 tat aag aat ctc ggt gct cac gtc gac gcg att acc atc cag aac gag  776
Tyr Lys Asn Leu Gly Ala His Val Asp Ala Ile Thr Ile Gln Asn Glu
 205                 210                 215 ccg ctg ttc agc tca gcg ggc tat ccc acc atg tat gtc tac gat tat  824
Pro Leu Phe Ser Ser Ala Gly Tyr Pro Thr Met Tyr Val Tyr Asp Tyr
220                 225                 230                 235 gag tcg gca cag ctg atc cag aac tac atc ggc ccc gct ctt gcc agc  872
Glu Ser Ala Gln Leu Ile Gln Asn Tyr Ile Gly Pro Ala Leu Ala Ser
             240                 245                 250 gcg ggg cta gat acg gaa atc tgg gct tat gac cac aac aca gat gtc  920
Ala Gly Leu Asp Thr Glu Ile Trp Ala Tyr Asp His Asn Thr Asp Val
         255                 260                 265 ccg tcg tac ccc cag act gtc ctt aac cag gcc ggt cag tac gtc aag  968
Pro Ser Tyr Pro Gln Thr Val Leu Asn Gln Ala Gly Gln Tyr Val Lys
     270                 275                 280
```

-continued

```
tcg gtg gcc tg cac tgc tac gct ccc aac gtc gac tgg acc gtg ctc    1016
Ser Val Ala Trp His Cys Tyr Ala Pro Asn Val Asp Trp Thr Val Leu
    285                 290                 295 agc cag ttc cac aac aca aac cct gga gtgaag caa tat atg acc gag    1064
Ser Gln Phe His Asn Thr Asn Pro Gly Val Lys Gln Tyr Met Thr Glu
300                 305                 310                 315 tgc tgg act cca gca tct ggc gca tgg cat cag gcg gcg gac ttc acc   1112
Cys Trp Thr Pro Ala Ser Gly Ala Trp His Gln Ala Ala Asp Phe Thr
                320                 325                 330 atg ggt ccc ctg cag aac tgg gcc tcg gga gtg gca gca tgg act ctg   1160
Met Gly Pro Leu Gln Asn Trp Ala Ser Gly Val Ala Ala Trp Thr Leu
            335                 340                 345 gga acc aac gct cag gat ggt ccg cat ctg tcc act ggc ggc tgc gcg   1208
Gly Thr Asn Ala Gln Asp Gly Pro His Leu Ser Thr Gly Gly Cys Ala
        350                 355                 360 aca tgt caa ggc ttg gtg acc atc aac aac gga gga tac acg ctc aac   1256
Thr Cys Gln Gly Leu Val Thr Ile Asn Asn Gly Gly Tyr Thr Leu Asn
    365                 370                 375 acc gca tac tac atg atg gcg caa ttc agc aag ttc atg ccg cct ggt   1304
Thr Ala Tyr Tyr Met Met Ala Gln Phe Ser Lys Phe Met Pro Pro Gly
380                 385                 390                 395 gcg att gtg ctc aat ggc agt ggc agc tac acg tac tct ggc gga ggc   1352
Ala Ile Val Leu Asn Gly Ser Gly Ser Tyr Thr Tyr Ser Gly Gly Gly
                400                 405                 410 ggt atc cag tcc gtg gct tcc ttg aat ccc gat gga acc cgc act gtg   1400
Gly Ile Gln Ser Val Ala Ser Leu Asn Pro Asp Gly Thr Arg Thr Val
            415                 420                 425 gtt att gaa aac act ttt ggc aat gat gtc tat gtg act gtc act atg   1448
Val Ile Glu Asn Thr Phe Gly Asn Asp Val Tyr Val Thr Val Thr Met
        430                 435                 440 aag agc ggg cag aag tgg agt ggg aac gcc cct agc caa tcc gtg act   1496
Lys Ser Gly Gln Lys Trp Ser Gly Asn Ala Pro Ser Gln Ser Val Thr
    445                 450                 455 acc tgg gtt ctt cca tct gct tga aaagagtgta gtttcagatg gtta-       1550
gatatg
Thr Trp Val Leu Pro Ser Ala
460                 465 tattgaagag tagcgcttgg agacatcaat agcctttttc taattacatg tcgtg-     1610
cagct tccaaaaaaa aaaaaaaaaa aaaaaaaaaa aactcga                          1647

SEQ ID NO: 10

Met Arg Ile Ser Val Gly Ala Leu Leu Gly Leu Thr Ala Leu Ser His
1               5                   10                  15

Ala Thr Thr Glu Lys Arg Ala Ala Ser Ala Ser Ala Tyr Cys Ser Asn
                20                  25                  30

Ser Ala Gly Asn Tyr Lys Leu Ser Ser Ile Ala Ala Pro Val Gln Gly
            35                  40                  45

Ala Gly Asn Pro Gly Ser Glu Ser Thr Trp Gln Leu Thr Val Asp Asp
        50                  55                  60

Thr Ser Ser Gly His Lys Gln Thr Ile Val Gly Phe Gly Ala Ala Val
65                  70                  75                  80

Thr Asp Ala Thr Val Thr Ser Phe Asn Thr Leu Ser Ala Ser Val Leu
                85                  90                  95

Gln Asp Leu Leu Asn Lys Leu Met Thr Pro Ala Gly Ala Asn Phe Ala
            100                 105                 110

Leu Met Arg His Thr Ile Gly Ala Ser Asp Leu Ser Gly Asp Pro Ala
        115                 120                 125
```

-continued

```
Tyr Thr Tyr Asp Asp Asn Gly Gly Lys Ala Asp Pro Ser Leu Ser Gly
130                 135                 140

Phe Asn Leu Gly Asp Arg Gly Thr Ala Met Ala Lys Met Leu Ala Thr
145                 150                 155                 160

Met Lys Ser Leu Gln Pro Asn Leu Lys Ile Leu Gly Ser Pro Trp Ser
                165                 170                 175

Ala Pro Gly Trp Met Lys Leu Asn Gly Val Leu Asp Gly Asn Thr Asn
            180                 185                 190

Asn Asn Asn Leu Asn Asp Gly Tyr Leu Thr Ser Gly Gly Thr Gly Ser
        195                 200                 205

Thr Gly Tyr Ala Ser Gln Phe Ala Gln Tyr Phe Val Lys Tyr Ile Gln
    210                 215                 220

Ala Tyr Lys Asn Leu Gly Ala His Val Asp Ala Ile Thr Ile Gln Asn
225                 230                 235                 240

Glu Pro Leu Phe Ser Ser Ala Gly Tyr Pro Thr Met Tyr Val Tyr Asp
                245                 250                 255

Tyr Glu Ser Ala Gln Leu Ile Gln Asn Tyr Ile Gly Pro Ala Leu Ala
            260                 265                 270

Ser Ala Gly Leu Asp Thr Glu Ile Trp Ala Tyr Asp His Asn Thr Asp
        275                 280                 285

Val Pro Ser Tyr Pro Gln Thr Val Leu Asn Gln Ala Gly Gln Tyr Val
    290                 295                 300

Lys Ser Val Ala Trp His Cys Tyr Ala Pro Asn Val Asp Trp Thr Val
305                 310                 315                 320

Leu Ser Gln Phe His Asn Thr Asn Pro Gly Val Lys Gln Tyr Met Thr
                325                 330                 335

Glu Cys Trp Thr Pro Ala Ser Gly Ala Trp His Gln Ala Ala Asp Phe
            340                 345                 350

Thr Met Gly Pro Leu Gln Asn Trp Ala Ser Gly Val Ala Ala Trp Thr
        355                 360                 365

Leu Gly Thr Asn Ala Gln Asp Gly Pro His Leu Ser Thr Gly Gly Cys
    370                 375                 380

Ala Thr Cys Gln Gly Leu Val Thr Ile Asn Asn Gly Gly Tyr Thr Leu
385                 390                 395                 400

Asn Thr Ala Tyr Tyr Met Met Ala Gln Phe Ser Lys Phe Met Pro Pro
                405                 410                 415

Gly Ala Ile Val Leu Asn Gly Ser Gly Ser Tyr Thr Tyr Ser Gly Gly
            420                 425                 430

Gly Gly Ile Gln Ser Val Ala Ser Leu Asn Pro Asp Gly Thr Arg Thr
        435                 440                 445

Val Val Ile Glu Asn Thr Phe Gly Asn Asp Val Tyr Val Thr Val Thr
    450                 455                 460

Met Lys Ser Gly Gln Lys Trp Ser Gly Asn Ala Pro Ser Gln Ser Val
465                 470                 475                 480

Thr Thr Trp Val Leu Pro Ser Ala
                485
```

EXAMPLE 9

Confirmation of the Expression of β-Primeverosidase in Mold a) Construction of Expression Cassette In order to verify whether or not the cloned gene is the primeverosidase gene, expression of the thus obtained DNA was confirmed. Using an *Aspergillus oryzae* Taka-amylase gene-containing plasmid pTG-Taa (Kato M, Aoyama A, Naruse F, Kobayashi T and Tsukagoshi N (1997), An *Aspergillus nidulans* nuclear protein, An CP, involved in enhancement of Taka-amylase A gene expression binds to the CCAAT-containing taaG2, amdS and gatA promoters., *Mol. Gen. Genet.*, 254: 119–126) as the template, a fragment was obtained by amplifying it by PCR using a primer TAA5'

SEQ ID NO: 11 sense primer:
    5'-GGGCCTGCAGGAATTCATGGTGTT-3' and a primer TP3'

SEQ ID NO: 12 antisense primer:
    5'-CGAGCCGGGGTTTCCGTCCGCAGGCGTTGC-3'.

<PCR reaction solution>

| | |
|---|---|
| template DNA solution (50 µg/ml) | 1 µl |
| 50 µM sense primer | 1 µl |
| 50 µM antisense primer | 1 µl |
| sterilized water | 22 µl |
| Premix Taq (EX Taq Version TaKaRa) | 23 µl |

<PCR reaction conditions>

| | | |
|---|---|---|
| Stage 1: | denaturation (95° C., 1 minute) | 1 cycle |
| Stage 2: | denaturation (95° C., 1 minute) annealing (55° C., 1 minute) elongation (72° C., 1 minute) | 30 cycles |
| Stage 3: | elongation (72° C., 5 minutes) | 1 cycle |

Also, a fragment was obtained by amplifying it by PCR using the DNA-containing plasmid pAFPri as the template and using a primer dPC5'

SEQ ID NO: 13 sense primer:
    5'-GCAACGCCTGCGGACGGAAACCCCGGCTCG-3' and a primer PC3'

SEQ ID NO: 14 antisense primer:
    5'-GCGCAAGCTTGGAAGCTGCACGACATGTAA-3'.

In addition, after recovering and mixing respective fragments, a fragment was obtained by amplifying it by PCR using the primer TAA5' and primer PC3'. This fragment contains a sequence corresponding to a region of from the *Aspergillus oryzae* Taka-amylase promoter to the N-terminal 5th amino acid of the mature protein and a sequence corresponding to a region of from the N-terminal 28th amino acid (glycine) to the C-terminal of the mature β-primeverosidase protein. An Sse8387I site has been introduced into the upstream of the thus obtained fragment, and a HindIII site into its downstream. The fragment was recovered by treating with restriction enzymes Sse8387I and HindIII.

Regarding the terminator region, a fragment was obtained by amplifying it by PCR using pTG-Taa as the template and using a primer TAAH

SEQ ID NO: 15 sense primer:
    5'-GCGCAAGCTTTGAAGGGTGGAGAGT-3' and a primer TAA3'

SEQ ID NO: 16 antisense primer:
    5'-GCGCCCTGCAGGTCTAGAATTCCTAGTGGTT-3'.

A HindIII site has been introduced into the upstream of the thus obtained fragment, and an Sse8387I site into its downstream. The fragment was recovered by treating with restriction enzymes HindIII and Sse8387I.

A plasmid pTG1 containing orotidine-5'-phosphate decarboxylase gene (pyr4) as a marker gene (Kato M (1997), *Mol. Gen. Genet.*, 254: 119-126) was treated with the restriction enzyme Sse8387I and with alkaline phosphatase and then recovered.

Plasmids pAFPriE1 (forward direction to the direction of the marker gene) and pAFPriE2 (reverse direction) were obtained by connecting these 3 fragments.

b) Acquisition of Transformant

An orotidine-5'-phosphate decarboxylase (PyrG) producing strain *Aspergillus nidulans* G191 (Kato M (1997), *Mol. Gen. Genet.*, 254: 119-126) was inoculated into a complete medium (2% malt extract, 0.1% peptone, 2% glucose, 0.1% uridine, 2 µg/ml p-aminobenzoic acid, pH 6.5) and cultured at 30° C. for 18 hours on a shaker. The cells were collected by filtration, suspended in a protoplast solution (0.8 M NaCl, 10 mM $NaH_2PO_4$, 20 mM $CaCl_2$, 3.75 mg/ml Novozyme 234) and then treated at 30° C. for 1 hour on a shaker. The resulting protoplasts were recovered by filtration and centrifuged at 1,500 rpm for 5 minutes to obtain the protoplasts as the precipitate. This precipitate was suspended in 0.8 M NaCl solution and centrifuged at 1,500 rpm for 5 minutes to collect the precipitate. This was again suspended in 0.8 M NaCl/50 mM $CaCl_2$ solution and centrifuged at 1,500 rpm for 5 minutes to collect the precipitate. A protoplast solution was obtained by suspending this in an appropriate amount of 0.8 M NaCl/50 mM $CaCl_2$ solution. Next, 50 µl of this protoplast solution was mixed with 20 µg of a DNA solution and 12.5 µl of a PEG solution (25% PEG 6000/50 mM $CaCl_2$/10 mM Tris-HCl (pH 7.5)) and then allowed to stand for 20 minutes on ice. Next, 0.5 ml of PEG solution was added and then the mixture was allowed to stand for 5 minutes on ice. Next, 1 ml of 0.8 M NaCl/50 mM $CaCl_2$ solution was added and mixed. A 0.5 ml portion of this mixed solution was mixed with 15 ml of 2% agar-containing regeneration medium (0.6% $NaNO_3$, 11 mM $KH_2PO_4$, 7 mM KCl, 1.2 M sorbitol, 0.05% $MgSO_4.7H_{20}$, 1% glucose, 2 µg/ml p-aminobenzoic acid, pH 6.5) which had been incubated at 50° C. in advance, solidified in Petri dishes and then cultured at 37° C. for 3 days.

This was carried out on the plasmid DNA of each of pTG1, pAFPriE1 and pAFPriE2.

Colonies formed on the plates were isolated by single spore separation. A total of 15 transformant strains were obtained from pTG1, and 23 strains from pAFPriE1 and 13 strains from pAFPriE2.

c) Evaluation of Transformants

Evaluation of transformants was carried out on 8 strains obtained from pTG1, 18 strains from pAFPriE1 and 12 strains from pAFPriE2. Each transformant was inoculated into an enzyme production confirming medium (1% polypeptone, 0.5% $KH_2PO_4$, 0.1% $NaNO_3$, 0.05% $MgSO_4.7H_2O$, 2% maltose, 4 µg/ml p-aminobenzoic acid, 0.1% trace element solution) (Core DJ., *Biochem., Biophys. Acta*, 1996, vol., 113, pp. 51–56) and cultured at 30° C. for 96 hours on a shaker. The culture broths were sampled after 48, 72, and 96 hours and filtered, and the resulting filtrates were checked for the activity. The enzyme activity was not found in the transformants obtained from pTG1 and pAFPriE2 but the enzyme activity was confirmed in 5 transformant strains obtained from pAFPriE1.

EXAMPLE 10

Comparison with Plant Gene by a Hybridization Method

Using the gene of an enzyme similar to the tea-derived diglycosidase as the probe, an examination was carried out to know if a gene having a similar structure is present on the chromosome of the microorganisms in which the presence of diglycosidase had been confirmed by us. Preparation of gene fragment of an enzyme similar to the tea-derived diglycosidase was carried out with reference to the report by Sakata, Mizutani et al. (The 73rd Annual Meeting of Agricultural Chemical Society of Japan) and Japanese Patent Application No. Hei. 11-56299.

Preparation of microorganism-derived chromosome was carried out in the following manner.

Preparation of chromosomes from yeast and fungi was carried out in accordance with the method described in *Molecular and Cellular Biology*, Vol. 3, pp. 1430–1439 (1983). Preparation of chromosomal DNA from bacteria was carried out in accordance with the method of Saito and Mitsuura (*Biochim. Biophys. Acta*, Vol. 72, pp. 619–629, 1963). Preparation of chromosomal DNA from actinomycetes was carried out in accordance with the method of Iefuji et al. (*Biosci. Biotec. Biochem.*, Vol. 60, pp. 1331–1338, 1996).

A 10 μg portion of each of the thus obtained various chromosomal DNA preparations was digested with BamHI in the case of *Aspergillus fumigatus, Aspergillus oryzae, Aspergillus niger, Aspergillus aculaetus, Penicillium lilacinum, Penicillium decumbence, Penicillium multicolor, Talaromyces emersonii, Mortierella vinacea, Cryptococcus albidus, Corynebacterium ammoniagenes, Corynebacterium glutamicum, Microbacterium arborescens* and *Penicillium rugolosum*, or with EcoRI in the case of *Rhizopus oryzae, Rhizomucor pusillus, Rhizomucor miehei* and *Actinoplanes missouriensis*, and the resulting digest was applied to a 1% agarose gel electrophoresis. As a control, the gene fragment of an enzyme similar to the tea-derived diglycosidase used as the probe was also subjected to the same gel electrophoresis. After the electrophoresis, DNA samples were blotted on a nylon membrane and hybridization was carried out using a labeled gene fragment p of an enzyme similar to the tea-derived diglycosidase (structural gene moiety of matured plant primeverosidase gene) as the probe, using DIG System Kit (Boehringer Mannheim) in accordance with the instruction attached thereto. As a result, when the detection was carried out under hybridization conditions (5×SSC, 1% blocking agent, 0.1% N-lauroylsarcosine sodium, 0.02% SDS, 68° C., overnight) and washing conditions (6×SSC, 0.1% SDS, room temperature, 5 min.×2 and 6×SSC, 0.1% SDS, 45° C., 15 min.×2), a signal was obtained at a position where the plant gene was blotted, but the signal was not observed at any other position where the microorganism-derived genome was blotted. Thus, it is considered that the microorganism-derived diglycosidase gene has a structure which is different from the plant primeverosidase gene.

On the other hand, using the *Aspergillus fumigatus* IAM 2020 diglycosidase gene of the invention obtained in Example 8 as the probe, an examination was carried out by the same methods and conditions to know if a gene having a similar structure is present on the chromosome of the microorganisms in which the presence of diglycosidase had been confirmed by us. As a result, the signal was detected in these microorganisms.

In addition, it was able to detect the signal in *Aspergillus oryzae, Aspergillus niger, Aspergillus aculeatus, Penicillium multicolor, Penicillium lilacinum, Corynebacterium ammoniagenes* and *Corynebacterium glutamicum*, even under more stringent washing conditions (5×SSC, room temperature, 10 min. and 4×SSC, 68° C., 30 min.).

EXAMPLE 11

Activity of the Diglycosidase to Hydrolyze Isoflavone in Isoflavone Glycosides

As shown in the following table, glucosides and modified glucosides of acetylglucosides and malonylglucosides, are present in isoflavone glycosides. The activity of diglycosidase to hydrolyze the acetyl type and malonyl type glucosides, namely the aglycon releasing activity, was examined.

| Isoflavone | M. wt. | $R_1$ | $R_2$ | $R_3$ | Concentration |
|---|---|---|---|---|---|
| Glycitin | 446.4 | H | OCH$_3$ | H | 2 mM |
| Genistin | 432.4 | OH | H | H | 2 mM |
| Daidzin | 416.4 | H | H | H | 2 mM |
| Acetylglycitin | 458.4 | H | OCH$_3$ | COCH$_3$ | 2 mM |
| Acetylgenistin | 474.7 | OH | H | COCH$_3$ | 2 mM |
| Acetyldaidzin | 458.4 | H | H | COCH$_3$ | 2 mM |
| Malonylglycitin | 502.4 | H | OCH$_3$ | COCH$_2$COOH | 2 mM |
| Malonylgenistin | 518.4 | OH | H | COCH$_2$COOH | 2 mM |
| Malonyldaidzin | 502.4 | H | H | COCH$_2$COOH | 2 mM |

$R_1$ to $R_3$ correspond to the following structural formula.

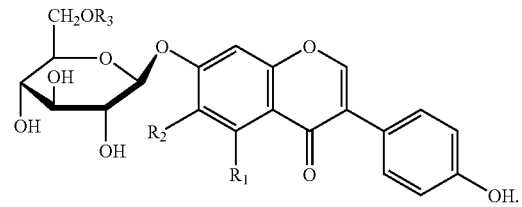

Each of acetylglycitin, acetylgenistin, acetyldaidzin, malonylglycitin, malonylgenistin and malonyldaidzin (produced by Fujicco, available from Nakalai Tesque) was allowed to react with a diglycosidase enzyme solution prepared from *Asp. fumigatus* or *Pen. multicolor* or with an almond-derived glucosidase (mfd. by Sigma) under the following conditions.

Each of the enzymes was diluted with 20 mM acetate buffer (pH 4.0) to adjust its activity to 1.88 AU/ml, and then 2 mM of each isoflavone (12.5 μg), 20 mM of acetate buffer (87.5 μl) and each enzyme solution (25 μl) were mixed to carry out the reaction at 55° C. After 1, 3 and 6 hours of the reaction, samples were taken out in 25 μl portions, and each of the samples was mixed with 75 μl of methanol and 900 μl of water, filtered through a filter (0.2 μm) and then further diluted 2.5 times with water. A 1 ml portion thereof was analyzed by HPLC (HPLC conditions; column: ODS 80TM (Tosoh), eluent: a mixed solution of acetonitrile and 10% acetic acid, separation under linear density gradient).

As a result, it was revealed that the glucosidase (Sigma) hardly hydrolyzed the modified glucoside substrates, but both diglycosidase enzymes hydrolyzed all of the modified glucosides efficiently and released the aglycon.

EXAMPLE 12

Preparation of an Aroma Component Precursor, Eugenyl Primeveroside

A 2 kg portion of fresh leaves of *Camellia sasanqua* were extracted with hot water at 100° C. for 10 minutes, and the extract was applied to a column packed with Diaion HP20

(mfd. by Mitsubishi Chemical) to adsorb eugenyl primeveroside thereon. The column was washed with about 2 times the bed volume of deionized water and 20% methanol and then the adsorbed eugenyl primeveroside was eluted with 100% methanol. Thereafter, the thus recovered methanol solution containing eugenyl primeveroside was concentrated to crystallize eugenyl primeveroside which was then recovered using a glass filter.

A 1 ml portion of the crude enzyme concentrate obtained in Example 4 was mixed with 1 ml of the eugenyl primeveroside solution adjusted to 5 mg/ml with 20 mM phosphate buffer (pH 6.0), the mixture was incubated at 37° C. for 24 hours and then the formation of aroma was examined by a sensory test (10 panel). As a result, formation of the eugenol-specific aroma was confirmed in all of the cases in which the crude enzyme concentrates of two *Aspergillus niger* strains and *Aspergillus fumigatus* were used.

In a case in which the crude enzyme concentrates were used after their heat-treatment (100° C., 10 minutes), the eugenol-specific aroma was not observed. Accordingly, it was found that these crude enzyme extracts have a function to release the aroma component aglycon from glycosides such as eugenyl primeveroside.

EXAMPLE 13

Release of Disaccharide from pNP-primeveroside by Purified Enzyme

A 0.3 AU portion of the purified enzyme solution obtained in Example 6 and the aforementioned pNP-primeveroside were incubated at 37° C. for 24 hours to examine release of disaccharide by TLC. As a result, a spot was observed at the same position of primeverose so that release of a disaccharide was confirmed. Such a spot was not found by the heat-treated purified enzyme solution used as a control. Thus, it was revealed that the purified enzyme has a function to release a disaccharide from a disaccharide glycoside.

EXAMPLE 14

Release of Disaccharide and Formation of Aroma from Eugenyl Primeveroside by Purified Enzyme A 0.3 AU portion of the purified enzyme solution obtained in Example 6 and the aforementioned pNP-primeveroside were incubated at 37° C. for 24 hours to examine release of disaccharide by TLC. As a result, a spot was observed at the same position of primeverose so that release of a disaccharide was confirmed. In addition, when the reaction solution was analyzed by a gas chromatography, release of eugenol as the aglycon of eugenyl primeveroside glycoside was confirmed, and the release of eugenol was also confirmed by a sensory test. These were not found in heat-inactivated enzyme solution. Thus, it was revealed that the purified enzyme forms aroma by acting upon an aroma precursor such as eugenyl primeveroside.

EXAMPLE 15

Release of Disaccharide from Pigment Glycoside

Release of disaccharide was examined using a disaccharide glycoside, ruberythric acid, as the substrate. Ruberythric acid was prepared by adsorbing a water extract of *Rubia tinctorum* L. root powder for staining use (available from Tanaka Senshoku Ten) to HP-20 column, washing the column with 50% methanol, and then eluting the compound with 100% methanol and evaporating the eluate to dryness using an evaporator. A substrate prepared by dissolving the thus recovered ruberythric acid in a phosphate buffer to a concentration of 5 mg/ml was mixed with the crude enzyme solution (0.3 AU) shown in Example 4 or the purified enzyme solution shown in Example 6 and incubated at 37° C. for 24 hours, and then the reaction solution was analyzed by TLC. As a result, release of the disaccharide primeverose and the aglycon alizarin was observed by the crude enzyme solution and purified enzyme solution.

Using the diglycosidase preparations derived from various microorganisms shown in Example 5, their ability to hydrolyze various disaccharide glycosides was examined using TLC. As a result, it was revealed that the diglycosidase acts upon not only the primeveroside glycosides but also various other disaccharide glycosides analogous to the primeveroside glycosides, including rutinose glycosides such as naringin and rutin, gentiobiose glycosides, arabinofuranosyl glycosides and apiofuranosyl glycosides, and thereby releases disaccharides and produces respective free aglycons.

EXAMPLE 17

Improvement of Tea Extract Aroma

Using the *Aspergillus fumigatus* enzyme solutions shown in Examples 4 and 6, their function to increase aroma components of green tea, black tea and oolong tea was examined. Each tea extract was mixed with 1.88 AU of the enzyme and incubated at 55° C. for 24 hours and then increase in the aroma was examined by a gas chromatography under the aforementioned conditions. As a result, it was found that aroma components such as 1-hexanol, 3-hexen-1-ol, benzaldehyde, linalool, methyl salicyanate, geraniol and benzyl alcohol were increased. Increase in the aroma was also found by a sensory test.

EXAMPLE 18

Improvement of Fruit Juice Aroma

Using the *Aspergillus fumigatus* and *Penicillium multicolor* enzyme solutions shown in Examples 4 and 5, 1.88 AU of each of the enzyme was added to a fruit juice such as of grape, orange, apple, prune or nectar and incubated at 37° C. for 24 hours and then the aroma was analyzed by a gas chromatography. As a result, increase in the aroma components such as linalool was observed. Improvement of the aroma was also found in the enzyme-treated fruit juices by a sensory test.

EXAMPLE 19

Improvement of Wine Aroma

Using the various crude enzyme solutions shown in Example 4, 0.5 AU of each enzyme was added to red wine and white wine and incubated at 37° C. for 24 hours to examine improvement of the aroma by a sensory test. As a result, improvement of the aroma was found in both cases.

EXAMPLE 20

When 1 ml of each of the various crude enzyme concentrates obtained in Examples 4 and 5 was mixed with 1 ml of a grape juice (commercial product: 100% fruit juice, concentrated and reduced) and then incubated at 37° C. overnight (14 hours) to examine the aroma, the aroma was clearly improved in comparison with a sample in which an acetate buffer was added instead of the enzyme preparation. In addition, this function was not found when the crude enzyme concentrate was heat-treated at 100° C. for 10 minutes.

EXAMPLE 21

A 1 ml portion of each of the crude enzyme concentrates obtained in Example 4 was mixed with 1 ml of a commercially available orange juice (reduced concentrate) and incubated at 37° C. for 24 hours to examine formation of the aroma by a sensory test. As a result, improving effect of the aroma of the orange juice was found in the crude enzyme concentrates derived from the two *Aspergillus niger* strains and *Aspergillus fumigatus*. Such a function was not found when the crude enzyme concentrate was heat-treated (100° C., 10 minutes).

EXAMPLE 22

An examination was carried out to find whether a sugar transfer in disaccharide unit is generated by diglycosidase.

The purified enzyme of Example 6 was diluted with deionized water to adjust the activity to E1.0 AU/ml, and acetonitrile (200 ml) containing 2.5% phenethyl alcohol, 20 mM acetate buffer (250 μl) containing 10% primeverose and the enzyme solution (50 μl) were mixed to carry out the reaction at 55° C. The reaction was completed after 6 hours and the reaction solution was mixed with 500 μl of diethyl ether, stirred and then centrifuged to remove free aglycon which was transferred into the ether layer. By applying the water layer to a Diaion HP-20 column and passing purified water through the column, free primeverose was removed. The disaccharide glycoside adsorbed to the resin was eluted with methanol and concentrated to dryness. This was dissolved in 100 μl of deionized water, and a 20 μl portion thereof was spotted on a TLC plate to detect the reaction product (the developing solvent was ethyl acetate:acetic acid:deionized water=3:1:1, acetic acid:methanol=1:4 solution was sprayed thereto after the development and allowed to stand at 105° C. for 10 minutes).

As a result, it was revealed that β-primeverosidase transfers the diglycoside to phenethyl alcohol and thereby forms a disaccharide glycoside.

INDUSTRIAL APPLICABILITY

An enzyme having a function to cut β-primeveroside and/or analogous disaccharide glycoside in disaccharide unit or to hydrolyze modified glucosides can be provided by the invention as a novel enzyme using microorganisms as its supply source, and it can be broadly used in various types of food, medicaments, quasi drugs and the like by using the enzyme composition of the invention. For example, the aroma, pigment and physiologically active component of food can be increased or decreased.

The invention claimed is:

1. An isolated polypeptide comprising the amino acid sequence of SEQ ID NO:8.

2. An isolated polypeptide consisting of the amino acid sequence of SEQ ID NO:8.

* * * * *

SEQUENCE LISTING

```
<160> NUMBER OF SEQ ID NOS: 16

<210> SEQ ID NO 1
<211> LENGTH: 22
<212> TYPE: PRT
<213> ORGANISM: Aspergillus fumigatus

<400> SEQUENCE: 1

Ala Ala Ser Ala Ser Ala Tyr Cys Ser Asn Ser Ala Gly Asn Tyr Lys
1               5                   10                  15

Leu Ser Ser Ile Ala Ala
            20

<210> SEQ ID NO 2
<211> LENGTH: 22
<212> TYPE: PRT
<213> ORGANISM: Aspergillus fumigatus

<400> SEQUENCE: 2

Leu Met Thr Pro Ala Gly Ala Asn Phe Ala Leu Met Arg His Thr Ile
1               5                   10                  15

Gly Ala Ser Asp Leu Ser
            20

<210> SEQ ID NO 3
<211> LENGTH: 28
<212> TYPE: DNA
<213> ORGANISM: Artificial Sequence
<220> FEATURE:
<223> OTHER INFORMATION: synthetic DNA
<221> NAME/KEY: misc_feature
<222> LOCATION: (14)..(14)
<223> OTHER INFORMATION: "n" may be a c, g or t
<221> NAME/KEY: misc_feature
<222> LOCATION: (17)..(17)
<223> OTHER INFORMATION: "n" may be a c, g or t
<221> NAME/KEY: misc_feature
<222> LOCATION: (20)..(20)
<223> OTHER INFORMATION: "n" may be a c, g or t
```

<400> SEQUENCE: 3
acgaattcaa ywsngcnggn aaytayaa                                          28

<210> SEQ ID NO 4
<211> LENGTH: 28
<212> TYPE: DNA
<213> ORGANISM: Artificial Sequence
<220> FEATURE:
<223> OTHER INFORMATION: synthetic DNA
<221> NAME/KEY: misc_feature
<222> LOCATION: (17)..(17)
<223> OTHER INFORMATION: "n" may be a c, g or t
<221> NAME/KEY: misc_feature
<222> LOCATION: (23)..(23)
<223> OTHER INFORMATION: "n" may be a c, g or t
<221> NAME/KEY: misc_feature
<222> LOCATION: (26)..(26)
<223> OTHER INFORMATION: "n" may be a c, g or t

<400> SEQUENCE: 4
cggaattcta ytgywsnaay wsngcngg                                          28

<210> SEQ ID NO 5
<211> LENGTH: 28
<212> TYPE: DNA
<213> ORGANISM: Artificial Sequence
<220> FEATURE:
<223> OTHER INFORMATION: synthetic DNA
<221> NAME/KEY: misc_feature
<222> LOCATION: (17)..(17)
<223> OTHER INFORMATION: "n" may be a c, g or t
<221> NAME/KEY: misc_feature
<222> LOCATION: (20)..(20)
<223> OTHER INFORMATION: "n" may be a c, g or t
<221> NAME/KEY: misc_feature
<222> LOCATION: (23)..(23)
<223> OTHER INFORMATION: "n" may be a c, g or t
<221> NAME/KEY: misc_feature
<222> LOCATION: (26)..(26)
<223> OTHER INFORMATION: "n" may be a c, g or t

<400> SEQUENCE: 5
tcaagcttgc raarttngcn ccngcngg                                          28

<210> SEQ ID NO 6
<211> LENGTH: 28
<212> TYPE: DNA
<213> ORGANISM: Artificial Sequence
<220> FEATURE:
<223> OTHER INFORMATION: synthetic DNA
<221> NAME/KEY: misc_feature
<222> LOCATION: (11)..(11)
<223> OTHER INFORMATION: "n" may be a c, g or t
<221> NAME/KEY: misc_feature
<222> LOCATION: (17)..(17)
<223> OTHER INFORMATION: "n" may be a c, g or t
<221> NAME/KEY: misc_feature
<222> LOCATION: (23)..(23)
<223> OTHER INFORMATION: "n" may be a c, g or t

<400> SEQUENCE: 6
agaagcttgc nccdatngtr tgnckcat                                          28

<210> SEQ ID NO 7
<211> LENGTH: 1401
<212> TYPE: DNA
<213> ORGANISM: Aspergillus fumigatus

<400> SEQUENCE: 7
gccgcctctg cttcggctta ctgttccaac tcggccggca actacaagct gtcctccatc      60

```
gcagctccgg ttcaagggc cggaaacccc ggctcggaat cgacctggca attgaccgtt    120
gacgacactt cgtccggtca caaacagacg atagttgggt tcggtgctgc tgtcactgat    180
gccacggtca cctcgttcaa cactttgtcc gcctccgtgc tgcaagactt gctcaataaa    240
ctgatgacac ctgccggggc gaactttgct ttgatgcgac atactattgg ggcttcggat    300
ctgtccggtg acccagccta cacgtacgat gacaatggtg ggaaagcgga tccgtcactg    360
tcgggattca acctggggga ccgcggaacg gctatggcca agatgttggc aacaatgaag    420
tctctgcagc ccaacctcaa gatcctcggc tctccctgga gtgcaccagg atggatgaag    480
ctgaacgggg tccttgatgg caatacgaac aacaacaact gaacgatgg ataccctaacc    540 agtgggggaa ccggtagtac ggggtatgcc agtcaattcg cgcagtactt tgtcaagtac    600
attcaggcct ataagaatct cggtgctcac gtcgacgcga ttaccatcca gaacgagccg    660
ctgttcagct cagcgggcta tcccaccatg tatgtctacg attatgagtc ggcacagctg    720
atccagaact acatcggccc cgctcttgcc agcgcggggc tagatacgga aatctgggct    780
tatgaccaca acacagatgt cccgtcgtac ccccagactg tccttaacca ggccggtcag    840
tacgtcaagt cggtggcctg gcactgctac gctcccaacg tcgactggac cgtgctcagc    900
cagttccaca acacaaaccc tggagtgaag caatatatga ccgagtgctg gactccagca    960
tctggcgcat ggcatcaggc ggcggacttc accatgggtc ccctgcagaa ctgggcctcg    1020
ggagtggcag catggactct gggaaccaac gctcaggatg gtccgcatct gtccactggc    1080
ggctgcgcga catgtcaagg cttggtgacc atcaacaacg gaggatacac gctcaacacc    1140
gcatactaca tgatggcgca attcagcaag ttcatgccgc ctggtgcgat tgtgctcaat    1200
ggcagtggca gctacacgta ctctggcgga ggcggtatcc agtccgtggc ttccttgaat    1260
cccgatggaa cccgcactgt ggttattgaa aacacttttg gcaatgatgt ctatgtgact    1320
gtcactatga gagcgggca gaagtggagt gggaacgccc ctagccaatc cgtgactacc    1380
tgggttcttc catctgcttg a                                               1401
```

<210> SEQ ID NO 8
<211> LENGTH: 466
<212> TYPE: PRT
<213> ORGANISM: Aspergillus fumigatus

<400> SEQUENCE: 8

```
Ala Ala Ser Ala Ser Ala Tyr Cys Ser Asn Ser Ala Gly Asn Tyr Lys
1               5                   10                  15

Leu Ser Ser Ile Ala Ala Pro Val Gln Gly Ala Gly Asn Pro Gly Ser
                20                  25                  30

Glu Ser Thr Trp Gln Leu Thr Val Asp Asp Thr Ser Ser Gly His Lys
            35                  40                  45

Gln Thr Ile Val Gly Phe Gly Ala Ala Val Thr Asp Ala Thr Val Thr
        50                  55                  60

Ser Phe Asn Thr Leu Ser Ala Ser Val Leu Gln Asp Leu Leu Asn Lys
65                  70                  75                  80

Leu Met Thr Pro Ala Gly Ala Asn Phe Ala Leu Met Arg His Thr Ile
                85                  90                  95

Gly Ala Ser Asp Leu Ser Gly Asp Pro Ala Tyr Thr Tyr Asp Asp Asn
            100                 105                 110

Gly Gly Lys Ala Asp Pro Ser Leu Ser Gly Phe Asn Leu Gly Asp Arg
        115                 120                 125

Gly Thr Ala Met Ala Lys Met Leu Ala Thr Met Lys Ser Leu Gln Pro
```

```
                130                 135                 140
Asn Leu Lys Ile Leu Gly Ser Pro Trp Ser Ala Pro Gly Trp Met Lys
145                 150                 155                 160

Leu Asn Gly Val Leu Asp Gly Asn Thr Asn Asn Asn Leu Asn Asp
                165                 170                 175

Gly Tyr Leu Thr Ser Gly Gly Thr Gly Ser Thr Gly Tyr Ala Ser Gln
                180                 185                 190

Phe Ala Gln Tyr Phe Val Lys Tyr Ile Gln Ala Tyr Lys Asn Leu Gly
                195                 200                 205

Ala His Val Asp Ala Ile Thr Ile Gln Asn Glu Pro Leu Phe Ser Ser
210                 215                 220

Ala Gly Tyr Pro Thr Met Tyr Val Tyr Asp Tyr Glu Ser Ala Gln Leu
225                 230                 235                 240

Ile Gln Asn Tyr Ile Gly Pro Ala Leu Ala Ser Ala Gly Leu Asp Thr
                245                 250                 255

Glu Ile Trp Ala Tyr Asp His Asn Thr Asp Val Pro Ser Tyr Pro Gln
                260                 265                 270

Thr Val Leu Asn Gln Ala Gly Gln Tyr Val Lys Ser Val Ala Trp His
                275                 280                 285

Cys Tyr Ala Pro Asn Val Asp Trp Thr Val Leu Ser Gln Phe His Asn
290                 295                 300

Thr Asn Pro Gly Val Lys Gln Tyr Met Thr Glu Cys Trp Thr Pro Ala
305                 310                 315                 320

Ser Gly Ala Trp His Gln Ala Ala Asp Phe Thr Met Gly Pro Leu Gln
                325                 330                 335

Asn Trp Ala Ser Gly Val Ala Ala Trp Thr Leu Gly Thr Asn Ala Gln
                340                 345                 350

Asp Gly Pro His Leu Ser Thr Gly Gly Cys Ala Thr Cys Gln Gly Leu
                355                 360                 365

Val Thr Ile Asn Asn Gly Gly Tyr Thr Leu Asn Thr Ala Tyr Tyr Met
370                 375                 380

Met Ala Gln Phe Ser Lys Phe Met Pro Pro Gly Ala Ile Val Leu Asn
385                 390                 395                 400

Gly Ser Gly Ser Tyr Thr Tyr Ser Gly Gly Gly Ile Gln Ser Val
                405                 410                 415

Ala Ser Leu Asn Pro Asp Gly Thr Arg Thr Val Val Ile Glu Asn Thr
                420                 425                 430

Phe Gly Asn Asp Val Tyr Val Thr Val Thr Met Lys Ser Gly Gln Lys
                435                 440                 445

Trp Ser Gly Asn Ala Pro Ser Gln Ser Val Thr Thr Trp Val Leu Pro
450                 455                 460

Ser Ala
465

<210> SEQ ID NO 9
<211> LENGTH: 1647
<212> TYPE: DNA
<213> ORGANISM: Aspergillus fumigatus
<220> FEATURE:
<221> NAME/KEY: CDS
<222> LOCATION: (54)..(1517)
<223> OTHER INFORMATION:
<221> NAME/KEY: mat_peptide
<222> LOCATION: (120)..()
<223> OTHER INFORMATION:

<400> SEQUENCE: 9
```

|  |  |
|---|---|
| ggcgacacca gaaagcaacc aagagcacga cacggactta tttctctttg aca atg<br>                                                                                         Met | 56 |
| cgt ata tct gtc ggt gct ctg ctt ggc ttg aca gcc ctg agt cat gcc<br>Arg Ile Ser Val Gly Ala Leu Leu Gly Leu Thr Ala Leu Ser His Ala<br> -20                     -15                     -10 | 104 |
| aca aca gag aaa cga gcc gcc tct gct tcg gct tac tgt tcc aac tcg<br>Thr Thr Glu Lys Arg Ala Ala Ser Ala Ser Ala Tyr Cys Ser Asn Ser<br> -5                -1  1             5                     10 | 152 |
| gcc ggc aac tac aag ctg tcc tcc atc gca gct ccg gtt caa ggg gcc<br>Ala Gly Asn Tyr Lys Leu Ser Ser Ile Ala Ala Pro Val Gln Gly Ala<br>                15                      20                     25 | 200 |
| gga aac ccc ggc tcg gaa tcg acc tgg caa ttg acc gtt gac gac act<br>Gly Asn Pro Gly Ser Glu Ser Thr Trp Gln Leu Thr Val Asp Asp Thr<br>          30                      35                     40 | 248 |
| tcg tcc ggt cac aaa cag acg ata gtt ggg ttc ggt gct gct gtc act<br>Ser Ser Gly His Lys Gln Thr Ile Val Gly Phe Gly Ala Ala Val Thr<br>       45                     50                     55 | 296 |
| gat gcc acg gtc acc tcg ttc aac act ttg tcc gcc tcc gtg ctg caa<br>Asp Ala Thr Val Thr Ser Phe Asn Thr Leu Ser Ala Ser Val Leu Gln<br>60                   65                     70                     75 | 344 |
| gac ttg ctc aat aaa ctg atg aca cct gcc ggg gcg aac ttt gct ttg<br>Asp Leu Leu Asn Lys Leu Met Thr Pro Ala Gly Ala Asn Phe Ala Leu<br>                80                      85                     90 | 392 |
| atg cga cat act att ggg gct tcg gat ctg tcc ggt gac cca gcc tac<br>Met Arg His Thr Ile Gly Ala Ser Asp Leu Ser Gly Asp Pro Ala Tyr<br>             95                    100                   105 | 440 |
| acg tac gat gac aat ggt ggg aaa gcg gat ccg tca ctg tcg gga ttc<br>Thr Tyr Asp Asp Asn Gly Gly Lys Ala Asp Pro Ser Leu Ser Gly Phe<br>      110                   115                   120 | 488 |
| aac ctg ggg gac cgc gga acg gct atg gcc aag atg ttg gca aca atg<br>Asn Leu Gly Asp Arg Gly Thr Ala Met Ala Lys Met Leu Ala Thr Met<br>125                    130                   135 | 536 |
| aag tct ctg cag ccc aac ctc aag atc ctc ggc tct ccc tgg agt gca<br>Lys Ser Leu Gln Pro Asn Leu Lys Ile Leu Gly Ser Pro Trp Ser Ala<br>140                    145                   150               155 | 584 |
| cca gga tgg atg aag ctg aac ggg gtc ctt gat ggc aat acg aac aac<br>Pro Gly Trp Met Lys Leu Asn Gly Val Leu Asp Gly Asn Thr Asn Asn<br>                160                   165                 170 | 632 |
| aac aac ttg aac gat gga tac cta acc agt ggg gga acc ggt agt acg<br>Asn Asn Leu Asn Asp Gly Tyr Leu Thr Ser Gly Gly Thr Gly Ser Thr<br>               175                   180                 185 | 680 |
| ggg tat gcc agt caa ttc gcg cag tac ttt gtc aag tac att cag gcc<br>Gly Tyr Ala Ser Gln Phe Ala Gln Tyr Phe Val Lys Tyr Ile Gln Ala<br>      190                 195                   200 | 728 |
| tat aag aat ctc ggt gct cac gtc gac gcg att acc atc cag aac gag<br>Tyr Lys Asn Leu Gly Ala His Val Asp Ala Ile Thr Ile Gln Asn Glu<br>205                    210                   215 | 776 |
| ccg ctg ttc agc tca gcg ggc tat ccc acc atg tat gtc tac gat tat<br>Pro Leu Phe Ser Ser Ala Gly Tyr Pro Thr Met Tyr Val Tyr Asp Tyr<br>220                    225                   230               235 | 824 |
| gag tcg gca cag ctg atc cag aac tac atc ggc ccc gct ctt gcc agc<br>Glu Ser Ala Gln Leu Ile Gln Asn Tyr Ile Gly Pro Ala Leu Ala Ser<br>                240                   245                 250 | 872 |
| gcg ggg cta gat acg gaa atc tgg gct tat gac cac aac aca gat gtc<br>Ala Gly Leu Asp Thr Glu Ile Trp Ala Tyr Asp His Asn Thr Asp Val<br>               255                   260                 265 | 920 |
| ccg tcg tac ccc cag act gtc ctt aac cag gcc ggt cag tac gtc aag<br>Pro Ser Tyr Pro Gln Thr Val Leu Asn Gln Ala Gly Gln Tyr Val Lys<br>      270                 275                   280 | 968 |
| tcg gtg gcc tgg cac tgc tac gct ccc aac gtc gac tgg acc gtg ctc | 1016 |

| | | | | | | | | | | | | |
|---|---|---|---|---|---|---|---|---|---|---|---|---|
| Ser | Val | Ala | Trp | His | Cys | Tyr | Ala | Pro | Asn | Val | Asp | Trp Thr Val Leu |
| | 285 | | | | 290 | | | | | 295 | | |

```
agc cag ttc cac aac aca aac cct gga gtg aag caa tat atg acc gag    1064
Ser Gln Phe His Asn Thr Asn Pro Gly Val Lys Gln Tyr Met Thr Glu
300             Phe His Asn     305                 310                 315 tgc tgg act cca gca tct ggc gca tgg cat cag gcg gcg gac ttc acc    1112
Cys Trp Thr Pro Ala Ser Gly Ala Trp His Gln Ala Ala Asp Phe Thr
                    320                 325                 330 atg ggt ccc ctg cag aac tgg gcc tcg gga gtg gca gca tgg act ctg    1160
Met Gly Pro Leu Gln Asn Trp Ala Ser Gly Val Ala Ala Trp Thr Leu
                335                 340                 345 gga acc aac gct cag gat ggt ccg cat ctg tcc act ggc ggc tgc gcg    1208
Gly Thr Asn Ala Gln Asp Gly Pro His Leu Ser Thr Gly Gly Cys Ala
            350                 355                 360 aca tgt caa ggc ttg gtg acc atc aac aac gga gga tac acg ctc aac    1256
Thr Cys Gln Gly Leu Val Thr Ile Asn Asn Gly Gly Tyr Thr Leu Asn
365                 370                 375 acc gca tac tac atg atg gcg caa ttc agc aag ttc atg ccg cct ggt    1304
Thr Ala Tyr Tyr Met Met Ala Gln Phe Ser Lys Phe Met Pro Pro Gly
380                 385                 390                 395 gcg att gtg ctc aat ggc agt ggc agc tac acg tac tct ggc gga ggc    1352
Ala Ile Val Leu Asn Gly Ser Gly Ser Tyr Thr Tyr Ser Gly Gly Gly
                400                 405                 410 ggt atc cag tcc gtg gct tcc ttg aat ccc gat gga acc cgc act gtg    1400
Gly Ile Gln Ser Val Ala Ser Leu Asn Pro Asp Gly Thr Arg Thr Val
            415                 420                 425 gtt att gaa aac act ttt ggc aat gat gtc tat gtg act gtc act atg    1448
Val Ile Glu Asn Thr Phe Gly Asn Asp Val Tyr Val Thr Val Thr Met
        430                 435                 440 aag agc ggg cag aag tgg agt ggg aac gcc cct agc caa tcc gtg act    1496
Lys Ser Gly Gln Lys Trp Ser Gly Asn Ala Pro Ser Gln Ser Val Thr
445                 450                 455 acc tgg gtt ctt cca tct gct tgaaaagagt gtagtttcag atggttagat       1547
Thr Trp Val Leu Pro Ser Ala
460             465 atgtattgaa gagtagcgct tggagacatc aatagccttt ttctaattac atgtcgtgca  1607
gcttccaaaa aaaaaaaaaa aaaaaaaaaa aaaaactcga                        1647

<210> SEQ ID NO 10
<211> LENGTH: 488
<212> TYPE: PRT
<213> ORGANISM: Aspergillus fumigatus

<400> SEQUENCE: 10

Met Arg Ile Ser Val Gly Ala Leu Leu Gly Leu Thr Ala Leu Ser His
        -20                 -15                 -10

Ala Thr Thr Glu Lys Arg Ala Ala Ser Ala Ser Ala Tyr Cys Ser Asn
    -5                  -1   1               5                   10

Ser Ala Gly Asn Tyr Lys Leu Ser Ser Ile Ala Ala Pro Val Gln Gly
                15                  20                  25

Ala Gly Asn Pro Gly Ser Glu Ser Thr Trp Gln Leu Thr Val Asp Asp
                30                  35                  40

Thr Ser Ser Gly His Lys Gln Thr Ile Val Gly Phe Gly Ala Ala Val
            45                  50                  55

Thr Asp Ala Thr Val Thr Ser Phe Asn Thr Leu Ser Ala Ser Val Leu
60                  65                  70

Gln Asp Leu Leu Asn Lys Leu Met Thr Pro Ala Gly Ala Asn Phe Ala
75                  80                  85                  90
```

Leu Met Arg His Thr Ile Gly Ala Ser Asp Leu Ser Gly Asp Pro Ala
            95                 100                 105

Tyr Thr Tyr Asp Asp Asn Gly Lys Ala Asp Pro Ser Leu Ser Gly
            110                 115                 120

Phe Asn Leu Gly Asp Arg Gly Thr Ala Met Ala Lys Met Leu Ala Thr
            125                 130                 135

Met Lys Ser Leu Gln Pro Asn Leu Lys Ile Leu Gly Ser Pro Trp Ser
        140                 145                 150

Ala Pro Gly Trp Met Lys Leu Asn Gly Val Leu Asp Gly Asn Thr Asn
155                 160                 165                 170

Asn Asn Asn Leu Asn Asp Gly Tyr Leu Thr Ser Gly Thr Gly Ser
            175                 180                 185

Thr Gly Tyr Ala Ser Gln Phe Ala Gln Tyr Phe Val Lys Tyr Ile Gln
            190                 195                 200

Ala Tyr Lys Asn Leu Gly Ala His Val Asp Ala Ile Thr Ile Gln Asn
            205                 210                 215

Glu Pro Leu Phe Ser Ser Ala Gly Tyr Pro Thr Met Tyr Val Tyr Asp
    220                 225                 230

Tyr Glu Ser Ala Gln Leu Ile Gln Asn Tyr Ile Gly Pro Ala Leu Ala
235                 240                 245                 250

Ser Ala Gly Leu Asp Thr Glu Ile Trp Ala Tyr Asp His Asn Thr Asp
            255                 260                 265

Val Pro Ser Tyr Pro Gln Thr Val Leu Asn Gln Ala Gly Gln Tyr Val
            270                 275                 280

Lys Ser Val Ala Trp His Cys Tyr Ala Pro Asn Val Asp Trp Thr Val
    285                 290                 295

Leu Ser Gln Phe His Asn Thr Asn Pro Gly Val Lys Gln Tyr Met Thr
    300                 305                 310

Glu Cys Trp Thr Pro Ala Ser Gly Ala Trp His Gln Ala Ala Asp Phe
315                 320                 325                 330

Thr Met Gly Pro Leu Gln Asn Trp Ala Ser Gly Val Ala Ala Trp Thr
            335                 340                 345

Leu Gly Thr Asn Ala Gln Asp Gly Pro His Leu Ser Thr Gly Gly Cys
            350                 355                 360

Ala Thr Cys Gln Gly Leu Val Thr Ile Asn Asn Gly Gly Tyr Thr Leu
            365                 370                 375

Asn Thr Ala Tyr Tyr Met Met Ala Gln Phe Ser Lys Phe Met Pro Pro
        380                 385                 390

Gly Ala Ile Val Leu Asn Gly Ser Gly Ser Tyr Thr Tyr Ser Gly Gly
395                 400                 405                 410

Gly Gly Ile Gln Ser Val Ala Ser Leu Asn Pro Asp Gly Thr Arg Thr
            415                 420                 425

Val Val Ile Glu Asn Thr Phe Gly Asn Asp Val Tyr Val Thr Val Thr
            430                 435                 440

Met Lys Ser Gly Gln Lys Trp Ser Gly Asn Ala Pro Ser Gln Ser Val
            445                 450                 455

Thr Thr Trp Val Leu Pro Ser Ala
    460                 465

<210> SEQ ID NO 11
<211> LENGTH: 24
<212> TYPE: DNA
<213> ORGANISM: Artificial Sequence
<220> FEATURE:
<223> OTHER INFORMATION: synthetic DNA

```
<400> SEQUENCE: 11
gggcctgcag gaattcatgg tgtt                                    24

<210> SEQ ID NO 12
<211> LENGTH: 30
<212> TYPE: DNA
<213> ORGANISM: Artificial Sequence
<220> FEATURE:
<223> OTHER INFORMATION: synthetic DNA

<400> SEQUENCE: 12
cgagccgggg tttccgtccg caggcgttgc                              30

<210> SEQ ID NO 13
<211> LENGTH: 30
<212> TYPE: DNA
<213> ORGANISM: Artificial Sequence
<220> FEATURE:
<223> OTHER INFORMATION: synthetic DNA

<400> SEQUENCE: 13
gcaacgcctg cggacggaaa ccccggctcg                              30

<210> SEQ ID NO 14
<211> LENGTH: 30
<212> TYPE: DNA
<213> ORGANISM: Artificial Sequence
<220> FEATURE:
<223> OTHER INFORMATION: synthetic DNA

<400> SEQUENCE: 14
gcgcaagctt ggaagctgca cgacatgtaa                              30

<210> SEQ ID NO 15
<211> LENGTH: 25
<212> TYPE: DNA
<213> ORGANISM: Artificial Sequence
<220> FEATURE:
<223> OTHER INFORMATION: synthetic DNA

<400> SEQUENCE: 15
gcgcaagctt tgaagggtgg agagt                                   25

<210> SEQ ID NO 16
<211> LENGTH: 31
<212> TYPE: DNA
<213> ORGANISM: Artificial Sequence
<220> FEATURE:
<223> OTHER INFORMATION: synthetic DNA

<400> SEQUENCE: 16
gcgccctgca ggtctagaat tcctagtggt t                            31
```